United States Patent
Kensey et al.

(10) Patent No.: US 6,322,525 B1
(45) Date of Patent: Nov. 27, 2001

(54) METHOD OF ANALYZING DATA FROM A CIRCULATING BLOOD VISCOMETER FOR DETERMINING ABSOLUTE AND EFFECTIVE BLOOD VISCOSITY

(75) Inventors: Kenneth Kensey, Chester Springs; William N. Hogenauer, Gilbertsville, both of PA (US); Young Cho, Cherry Hill, NJ (US)

(73) Assignee: Visco Technologies, Inc., Exton, PA (US)

( * ) Notice: Subject to any disclaimer, the term of this patent is extended or adjusted under 35 U.S.C. 154(b) by 0 days.

(21) Appl. No.: 09/501,856

(22) Filed: Feb. 10, 2000

Related U.S. Application Data

(63) Continuation-in-part of application No. 09/439,795, filed on Nov. 12, 1999, which is a continuation-in-part of application No. 08/919,906, filed on Aug. 28, 1997, now Pat. No. 6,019,735.

(51) Int. Cl.[7] .................................................. A61B 5/00
(52) U.S. Cl. .................................... 600/573; 73/1.73
(58) Field of Search .............................. 600/573, 578, 600/575, 574

(56) References Cited

U.S. PATENT DOCUMENTS

| H93 | 7/1986 | Matta et al. . |
|---|---|---|
| 1,810,992 | 6/1931 | Dallwitz-Wegner . |

(List continued on next page.)

FOREIGN PATENT DOCUMENTS

| 3138 514 | 4/1983 | (DE) . | |
|---|---|---|---|
| WO 94/20832 | 9/1994 | (DE) | 11/14 |
| 0 654 286 A1 | 12/1994 | (EP) | 5/1 |
| 2510257 | 1/1983 | (FR) . | |
| WO 99/10724 | 3/1999 | (WO) | 11/4 |
| WO 92/15878 | 9/1992 | (WO) | 33/49 |

OTHER PUBLICATIONS

Kensey, et al., Effects of whole blood viscosity On atherogenesis, Journal of Invasive Cardiology, vol. 9, 17, 1997.

(List continued on next page.)

*Primary Examiner*—Eric F. Winakur
*Assistant Examiner*—Pamela Wingood
(74) *Attorney, Agent, or Firm*—Caesar, Rivise, Bernstein, Cohen & Pokotilow, Ltd.

(57) ABSTRACT

A method is provided for detecting interactions in the circulating blood of a living being caused by external factors by analyzing the viscosity of the living being's circulating blood. The method utilizes a blood viscosity measuring system that monitors the change in height of two, oppositely-moving, columns of blood from the circulating blood of a patient and, given the dimensions of a capillary tube through which the blood flows, determines the blood viscosity over a range of shear rates, especially low shear rates. The system includes a tube set that includes a pair of riser tubes, a capillary tube of predetermined dimensions that is coupled between the riser tubes and a valve mechanism for controlling the circulating flow of blood from the patient into the riser tubes. Respective sensors monitor the movement of the columns of blood in each of the riser tubes and an associated microprocessor analyzes these movements, along with the predetermined dimensions of the capillary tube to determine the viscosity of the patient's circulating blood. A first viscosity profile is determined over a first shear rate range and a second viscosity profile is determined over the first shear rate range and a second shear rate range. The method utilizes the relationship of these two viscosity profiles, as well as with respect to a horizontal line, to detect the interactions in the circulating blood of a living being caused by the external factors. Furthermore, the tube set can then be pivoted clockwise and/or counterclockwise for measuring platelet aggregation and red blood cell deformability. In addition, a method and apparatus for determining the yield stress of the blood is discussed, as well as a method for determining the effects of drugs designed to treat a condition of the living being.

84 Claims, 9 Drawing Sheets

U.S. PATENT DOCUMENTS

| | | |
|---|---|---|
| 2,343,061 | 2/1944 | Irany . |
| 2,696,734 | 12/1954 | Brunstrum et al. . |
| 2,700,891 | 2/1955 | Shafer . |
| 2,934,944 | 5/1960 | Eolkin . |
| 3,071,961 | 1/1963 | Heigl et al. . |
| 3,116,630 | 1/1964 | Piros . |
| 3,137,161 | 6/1964 | Lewis et al. . |
| 3,138,950 | 6/1964 | Welty et al. . |
| 3,277,694 | 10/1966 | Cannon et al. . |
| 3,286,511 | 11/1966 | Harkness . |
| 3,342,063 | 9/1967 | Smythe et al. . |
| 3,435,665 | 4/1969 | Tzentis . |
| 3,520,179 | 7/1970 | Reed . |
| 3,604,247 | 9/1971 | Gramain et al. . |
| 3,666,999 | 5/1972 | Moreland, Jr. et al. . |
| 3,680,362 | 8/1972 | Geerdes et al. . |
| 3,699,804 | 10/1972 | Gassmann et al. . |
| 3,713,328 | 1/1973 | Aritomi . |
| 3,720,097 | 3/1973 | Kron . |
| 3,782,173 | 1/1974 | Van Vessem et al. . |
| 3,839,901 | 10/1974 | Finkle et al. . |
| 3,853,121 | 12/1974 | Mizrachy et al. . |
| 3,864,962 | 2/1975 | Stark et al. . |
| 3,908,441 | 9/1975 | Virloget . |
| 3,911,728 | 10/1975 | Fixot . |
| 3,952,577 | 4/1976 | Hayes et al. . |
| 3,967,934 | 7/1976 | Seitz et al. . |
| 3,990,295 | 11/1976 | Renovanz et al. . |
| 3,999,538 | 12/1976 | Philpot, Jr. . |
| 4,083,363 | 4/1978 | Philpot, Jr. . |
| 4,149,405 | 4/1979 | Ringrose . |
| 4,165,632 | 8/1979 | Weber et al. . |
| 4,193,293 | 3/1980 | Cavallari . |
| 4,207,870 | 6/1980 | Eldridge . |
| 4,302,965 | 12/1981 | Johnson et al. . |
| 4,341,111 | 7/1982 | Husar . |
| 4,417,584 | 11/1983 | Cathignol et al. . |
| 4,426,878 | 1/1984 | Price et al. . |
| 4,432,761 | 2/1984 | Dawe . |
| 4,461,830 | 7/1984 | Philpot, Jr. . |
| 4,517,830 | 5/1985 | Gunn et al. . |
| 4,519,239 | 5/1985 | Kiesewetter et al. . |
| 4,554,821 | 11/1985 | Kiesewetter et al. . |
| 4,616,503 | 10/1986 | Plungis et al. . |
| 4,637,250 | 1/1987 | Irvine, Jr. et al. . |
| 4,643,021 | 2/1987 | Mattout . |
| 4,680,957 | 7/1987 | Dodd . |
| 4,680,958 | 7/1987 | Ruelle et al. . |
| 4,750,351 | 6/1988 | Ball . |
| 4,856,322 | 8/1989 | Langrick et al. . |
| 4,858,127 | 8/1989 | Kron et al. . |
| 4,884,577 | 12/1989 | Merrill . |
| 4,899,575 | 2/1990 | Chu et al. . |
| 4,947,678 | 8/1990 | Hori et al. . |
| 5,099,698 | 3/1992 | Kath et al. . |
| 5,142,899 | 9/1992 | Park et al. . |
| 5,181,415 | 1/1993 | Esvan et al. . |
| 5,222,497 | 6/1993 | Ono . |
| 5,224,375 | 7/1993 | You et al. . |
| 5,257,529 | 11/1993 | Taniguchi et al. . |
| 5,271,398 | 12/1993 | Schlain et al. . |
| 5,272,912 | 12/1993 | Katsuzaki . |
| 5,327,778 | 7/1994 | Park . |
| 5,333,497 | 8/1994 | Brnd et al. . |
| 5,365,776 | 11/1994 | Lehmann et al. . |
| 5,421,328 | 6/1995 | Bedingham . |
| 5,443,078 | 8/1995 | Uflacker . |
| 5,447,440 | 9/1995 | Davis et al. . |
| 5,491,408 | 2/1996 | Rousseau . |
| 5,494,639 | 2/1996 | Grzegorzewski . |
| 5,549,119 | 8/1996 | Solar . |
| 5,629,209 | 5/1997 | Braun, Sr. et al. . |
| 5,686,659 | 11/1997 | Neel et al. . |
| 5,725,563 | 3/1998 | Klotz . |
| 5,792,660 | 8/1998 | Spillert et al. . |
| 5,837,885 | 11/1998 | Goodbread et al. . |
| B1 3,999,538 | 7/1984 | Philpot, Jr. . |

OTHER PUBLICATIONS

Leonhardt, et al., Studies of Plasma Viscosity in Primary Hyperlipoproteinaemia, Atherosclerosis, vol. 28, 29–40, 1977.

Ernst, et al., Cardiovascular Risk Factors and Hemorheology: Physical fitness, Stress and Obesity, Atherosclerosis, vol. 59, 263–269, 1986.

Levenson, et al., Cigarette Smoking and Hypertension, Atherosclerosis, vol. 7, 572–577, 1987.

Rillaerts, et al., Blood Viscosity in Human Obesity; relation to glucose Tolerance and Insulin Status, International Journal of Obesity, vol. 13, 739–741, 1989.

Rosenson, R., Viscosity and Ischemic Heart Disease, Journal of Vascular Medicine & Biology, vol. 4, 206–212, 1993.

Letcher, et al., Direct Relationship Between Blood Pressure and Blood Viscosity in Normal and Hypertensive Subjects, Am. Journal of Medicine vol. 70, 1195–1203, Jun., 1981.

Zwick, K.J., The Fluid Mechanics of Bonding With Yield Stress Exposies, Dissortation, Univ. of Pennsylvania, PA USA, 1–142, 1996.

Yarnell, et al., Fibrinogen, Viscosity, and White Blood Cell Count Are Major Risk Factors for Ischemic Heart Disease, Circulation, vol. 83, No. 3 Mar., 1991.

Tangney, et al., Postprandial changes in Plasma and Serum Viscosity And Plasma Lipids and Lipoproteins After an Acute Test Meal, American Jourrnal of Clinical Nutritiion, vol. 65, pp 36–40, 1997.

Seplowitz, et al., Effects of Lipoproteins on Plasma Viscosity, Atherosclerosis, vol. 38, pp. 89–95, 1981.

Rosenson, et al., Hyperviscosity Syndrome in a Hypercholesterolemic Patient with Primary Biliary Cirrhosis, Gastroenterology, Vi, 98, No. 5, 1990.

Lowe, et al., Blood Viscosity and Risk of Cardiovascular Events: the Edinburgh Artery Study, British Journal of Haematology, Vo. 96, 168–173, 1997.

Koenig, W., Blood Rheology Associated with Cardiovascular Risk Factors and Chronic Cardiovascular Diseases: Results of an Epidemiologic Cross–Sectional Study, Amer. College of Angiology, Paradise Island, Bahamas—Oct., 1987.

Hell, K., Importance of Blood Viscoelasticity in Arteriosclerosis, Intern'l College of Angiology, Montreux, Switzerland, Jul., 1987.

Delaunois, A., Thermal method for Continuous Blood–velocity Measurements in Large Blood Vessels, and Cardiac Output Determination, Medical and Biological Engineering, Marhc 1973, vol. 11, 201–205.

Nerem, et al., Fluid Mechanics in Atherosclerosis, Handbook of Bioengineering, Chap. 21, 20.24 to 21.22.

Litt, et al., Theory and Design of Disposable Clinical Blood Viscometer, Biorheology, Vo. 25, 697–712, 1988.

Cooke, et al., Automated Measurement of Plasma Viscosity by Capillary Viscometer, J. Clin. Pathology ,vol. 41, 1213–1216, 1988.

Jiminez, et al., A novel Computerized Viscometer/rheometer, Rev. Sci. Instrum. vol. 65, (1), pp. 229–241, Jan. 1994.

Harkness, A New Instrument for the Measurement of Plasma–Viscosity, The Lancet, New Inventions, pp. 280–281, Aug. 10, 1963.

Pringle, et al., Blood Viscosity and Raynaud's Disease, The Lancet, May, 1965.

Walker, et al., Measurement of Blood Viscosity using a conicylndrical viscometer, Medical and Biological Engineering, Sep., 1976.

Oguraa, et al., Measurement of Human Red Blood Cell Deformability Using A Single Micropore on a Thin $Si_3N_4$ Film, IEEE Transactions on Biomedical Engineering, vol. 38, No. 8, Aug., 1991.

Hausler, et al., A Newly Designed Oscillating Viscometer for Blood Viscosity Measurements, 1996, vol. 33, No. 4, Biorheology pp.397–404.

Martin, et al., Apparent Viscosity of Whole Human Blood at Various Hydrostatic Pressures I. Studies on Anticoagulated Blood Employing a New Capillary Viscometer, Biorheology, p. 3–12 1978, vol. 11.

Rheinhardt, et al., Rheologic Measurements on Small Samples With a New Capillary Viscometer, J. Lab. And Clinical Med., Dec. 1984 p. 921–931.

Chmiel, A New Capillary Viscometer For Clinical use, Biorheology p. 301–307 1979, vol. 12.

Pall Corporation, Pall BPF4 High Efficiency Leukocyte Removal Blood Processing Filter System, Pall Biomedical Products Corporation 1993.

Qamar, et al., The Goldman Algorithm Revisited: Prospective Evaluation of a Computer Derived Algorithm Versus Unaided Physician Judgment in Suspected Acute Myocardial Infarction, Am. Heart J. 138 vol. 4, 1999, pp 705–709.

METHOD OF ANALYZING DATA FROM A CIRCULATING BLOOD VISCOMETER FOR DETERMINING ABSOLUTE AND EFFECTIVE BLOOD VISCOSITY

RELATED APPLICATIONS

This application is a Continuation-in-Part of application Ser. No. 09/439,795, filed Nov. 12, 1999, entitled DUAL RISER/SINGLE VISCOMETER, which in turn is a Continuation-in-Part of application Ser. No. 08/919,906, filed Aug. 28, 1997 now U.S. Pat. No. 6,019,735, entitled VISCOSITY MEASURING APPARATUS AND METHOD OF USE, all of which are assigned to the same Assignee as the present invention and all of whose entire disclosures are incorporated by reference herein.

BACKGROUND OF THE INVENTION

This invention relates generally to a method for measuring the viscosity of blood, and more particularly, a method for measuring the absolute and effective viscosity of the circulating blood of a living being and over a wide range of shear rates.

The importance of determining the viscosity of blood is well-known. *Fibrogen, Viscosity and White Blood Cell Count Are Major Risk Factors for Ischemic Heart Disease*, by Yarnell et al., Circulation, Vol. 83, No. 3, March 1991; *Postprandial Changes in Plasma and Serum Viscosity and Plasma Lipids and Lipoproteins After an Acute Test Meal*, by Tangney, et al., American Journal for Clinical Nutrition, 65:36–40, 1997; *Studies of Plasma Viscosity in Primary Hyperlipoproteinaemia*, by Leonhardt et al., Atherosclerosis 28, 29–40, 1977; *Effects of Lipoproteins on Plasma Viscosity*, by Seplowitz, et al., Atherosclerosis 38, 89–95, 1981; *Hyperviscosity Syndrome in a Hypercholesterolemic Patient with Primary Biliary Cirrhosis*, Rosenson, et al., Gastroenterology, Vol. 98, No. 5, 1990; *Blood Viscosity and Risk of Cardiovascular Events:the Edinburgh Artery Study*, by Lowe et al., British Journal of Hematology, 96, 168–171, 1997; *Blood Rheology Associated with Cardiovascular Risk Factors and Chronic Cardiovascular Diseases: Results of an Epidemiologic Cross-Sectional Study*, by Koenig, et al., Angiology, The Journal of Vascular Diseases, November 1988; *Importance of Blood Viscoelasticity in Arteriosclerosis*, by Hell, et al., Angiology, The Journal of Vascular Diseases, June, 1989; *Thermal Method for Continuous Blood-Velocity Measurements in Large Blood Vessels, and Cardiac-Output Determination*, by Delanois, Medical and Biological Engineering, Vol. 11, No. 2, March 1973; *Fluid Mechanics in Atherosclerosis*, by Nerem, et al., Handbook of Bioengineering, Chapter 21, 1985.

Much effort has been made to develop apparatus and methods for determining the viscosity of blood. *Theory and Design of Disposable Clinical Blood Viscometer*, by Litt et al., Biorheology, 25, 697–712, 1988; *Automated Measurement of Plasma Viscosity by Capillary Viscometer*, by Cooke, et al., Journal of Clinical Pathology 41, 1213–1216, 1988; *A Novel Computerized Viscometer/Rheometer* by Jimenez and Kostic, Rev. Scientific Instruments 65, Vol 1, January 1994; *A New Instrument for the Measurement of Plasma-Viscosity*, by John Harkness, The Lancet, pp. 280–281, Aug. 10, 1963; *Blood Viscosity and Raynaud's Disease*, by Pringle, et al., The Lancet, pp. 1086–1089, May 22, 1965; *Measurement of Blood Viscosity Using a Conicylindrical Viscometer*, by Walker et al., Medical and Biological Engineering, pp. 551–557, September 1976.

One reference, namely, *The Goldman Algorithm Revisited: Prospective Evaluation of a Computer-Derived Algorithm Versus Unaided Physician Judgment in Suspected Acute Myocardial Infarction*, by Qamar, et al., Am Heart J 138(4):705–709, 1999, discusses the use of the Goldman algorithm for providing an indicator to acute myocardial infarction. The Goldman algorithm basically utilizes facts from a patient's history, physical examination and admission (emergency room) electrocardiogram to provide an AMI indicator.

In addition, there are a number of patents relating to blood viscosity measuring apparatus and methods. See for example, U.S. Pat. No. : 3,342,063 (Smythe et al.); U.S. Pat. No. 3,720,097 (Kron); U.S. Pat. No. 3,999,538 (Philpot, Jr.); U.S. Pat. No. 4,083,363 (Philpot); U.S. Pat. No. 4,149,405 (Ringrose); U.S. Pat. No. 4,165,632 (Weber, et. al.); U.S. Pat. No. 4,517,830 (Gunn, deceased, et. al.); U.S. Pat. No. 4,519,239 (Kiesewetter, et. al.); U.S. Pat. No. 4,554,821 (Kiesewetter, et. al.); U.S. Pat. No. 4,858,127 (Kron, et. al.); U.S. Pat. No. 4,884,577 (Merrill); U.S. Pat. No. 4,947,678 (Hori et al.); U.S. Pat. No. 5,181,415 (Esvan et al.); U.S. Pat. No. 5,257,529 (Taniguchi et al.); U.S. Pat. No. 5,271,398 (Schlain et al.); and U.S. Pat. No. 5,447,440 (Davis, et. al.).

The Smythe '063 patent discloses an apparatus for measuring the viscosity of a blood sample based on the pressure detected in a conduit containing the blood sample. The Kron '097 patent discloses a method and apparatus for determining the blood viscosity using a flowmeter, a pressure source and a pressure transducer. The Philpot '538 patent discloses a method of determining blood viscosity by withdrawing blood from the vein at a constant pressure for a predetermined time period and from the volume of blood withdrawn. The Philpot '363 patent discloses an apparatus for determining blood viscosity using a hollow needle, a means for withdrawing and collecting blood from the vein via the hollow needle, a negative pressure measuring device and a timing device. The Ringrose '405 patent discloses a method for measuring the viscosity of blood by placing a sample of it on a support and directing a beam of light through the sample and then detecting the reflected light while vibrating the support at a given frequency and amplitude. The Weber '632 patent discloses a method and apparatus for determining the fluidity of blood by drawing the blood through a capillary tube measuring cell into a reservoir and then returning the blood back through the tube at a constant flow velocity and with the pressure difference between the ends of the capillary tube being directly related to the blood viscosity. The Gunn '830 patent discloses an apparatus for determining blood viscosity that utilizes a transparent hollow tube, a needle at one end, a plunger at the other end for creating a vacuum to extract a predetermined amount and an apertured weight member that is movable within the tube and is movable by gravity at a rate that is a function of the viscosity of the blood. The Kiesewetter '239 patent discloses an apparatus for determining the flow shear stress of suspensions, principally blood, using a measuring chamber comprised of a passage configuration that simulates the natural microcirculation of capillary passages in a being. The Kiesewetter '821 patent discloses another apparatus for determining the viscosity of fluids, particularly blood, that includes the use of two parallel branches of a flow loop in combination with a flow rate measuring device for measuring the flow in one of the branches for determining the blood viscosity. The Kron '127 patent discloses an apparatus and method for determining blood viscosity of a blood sample over a wide range of shear rates. The Merrill '577 patent discloses an apparatus and method for determining the blood viscosity of a blood sample using a hollow column in fluid communication with a chamber containing a porous bed and means for measuring the blood flow rate within the column. The Hori '678 patent discloses a method for measurement of the viscosity change in blood by disposing a temperature sensor in the blood flow and stimulating the blood so as to cause a viscosity change. The Esvan '415 patent discloses an apparatus that detects the change in viscosity of a blood sample based on the relative slip of a drive element and a driven element, which holds the blood sample, that are rotated. The Taniguchi '529 patent discloses a method and apparatus for determining the viscosity of liquids, e.g., a blood sample, utilizing a pair of vertically-aligned tubes coupled together via fine tubes while using a pressure sensor to measure the change of an internal tube pressure with the passage of time and the change of flow rate of the blood. The Bedingham '328 patent discloses an intravascular blood parameter sensing system that uses a catheter and probe having a plurality of sensors (e.g., an $O_2$ sensor, $CO_2$ sensor, etc.) for measuring particular blood parameters in vivo. The Schlain '398 patent discloses a intra-vessel method and apparatus for detecting undesirable wwall effect on blood parameter sensors and for moving such sensors to reduce or eliminate the wall effect. The Davis '440 patent discloses an apparatus for conducting a variety of assays that are responsive to a change in the viscosity of a sample fluid, e.g., blood.

Viscosity measuring methods and devices for fluids in general are well-known. See for example, U.S. Pat. No. : 1,810,992 (Dallwitz-Wegner); U.S. Pat. No. 2,343,061 (Irany); U.S. Pat. No. 2,696,734 (Brunstrum et al.); U.S. Pat. No. 2,700,891 (Shafer); U.S. Pat. No. 2,934,944 (Eolkin); U.S. Pat. No. 3,071,961 (Heigl et al.); U.S. Pat. No. 3,116,630 (Piros); U.S. Pat. No. 3,137,161 (Lewis et al.); U.S. Pat. No. 3,138,950 (Welty et al.); U.S. Pat. No. 3,277,694 (Cannon et al.); U.S. Pat. No. 3,286,511 (Harkness); U.S. Pat. No. 3,435,665 (Tzentis); U.S. Pat. No. 3,520,179 (Reed); U.S. Pat. No. 3,604,247 (Gramain et al.); U.S. Pat. No. 3,666,999 (Moreland, Jr. et al.); U.S. Pat. No. 3,680,362 (Geerdes et al.); U.S. Pat. No. 3,699,804 (Gassmann et al.); U.S. Pat. No. 3,713,328 (Aritomi); U.S. Pat. No. 3,782,173 (Van Vessem et al.); U.S. Pat. No. 3,864,962 (Stark et al.); U.S. Pat. No. 3,908,441 (Virloget); U.S. Pat. No. 3,952,577 (Hayes et al.); U.S. Pat. No. 3,990,295 (Renovanz et al.); U.S. Pat. No. 4,149,405 (Ringrose); U.S. Pat. No. 4,302,965 (Johnson et al.); U.S. Pat. No. 4,426,878 (Price et al.); U.S. Pat. No. 4,432,761 (Dawe); U.S. Pat. No. 4,616,503 (Plungis et al.); U.S. Pat. No. 4,637,250 (Irvine, Jr. et al.); U.S. Pat. No. 4,680,957 (Dodd); U.S. Pat. No. 4,680,958 (Ruelle et al.); U.S. Pat. No. 4,750,351 (Ball); U.S. Pat. No. 4,856,322 (Langrick et al.); U.S. Pat. No. 4,899,575 (Chu et al.); U.S. Pat. No. 5,142,899 (Park et al.); U.S. Pat. No. 5,222,497 (Ono); U.S. Pat. No. 5,224,375 (You et al.); U.S. Pat. No. 5,257,529 (Taniguchi et al.); U.S. Pat. No. 5,327,778 (Park); and U.S. Pat. No. 5,365,776 (Lehmann et al.).

The following U.S. patents disclose viscosity or flow measuring devices, or liquid level detecting devices using optical monitoring: U.S. Pat. No. 3,908,441 (Virloget); U.S. Pat. No. 5,099,698 (Kath, et. al.); U.S. Pat. No. 5,333,497 (Br nd Dag A. et al.). The Virloget '441 patent discloses a device for use in viscometer that detects the level of a liquid in a transparent tube using photodetection. The Kath '698 patent discloses an apparatus for optically scanning a rotameter flow gauge and determining the position of a float therein. The Br nd Dag A. '497 patent discloses a method and apparatus for continuous measurement of liquid flow velocity of two risers by a charge coupled device (CCD) sensor.

U.S. Pat. No. 5,421,328 (Bedingham) discloses an intravascular blood parameter sensing system.

A statutory invention registration, H93 (Matta et al.) discloses an apparatus and method for measuring elongational viscosity of a test fluid using a movie or video camera to monitor a drop of the fluid under test.

The following publications discuss red blood cell deformability and/or devices used for determining such: *Measurement of Human Red Blood Cell Deformability Using a Single Micropore on a Thin $Si_3N_4$ Film*, by Ogura et al, IEEE Transactions on Biomedical Engineering, Vol. 38, No. 8, August 1991; *the Pall BPF4 High Efficiency Leukocyte Removal Blood Processing Filter System*, Pall Biomedical Products Corporation, 1993.

A device called the "Hevimet 40" has recently been advertised at www.hevimet.freeserve.co.uk. The Hevimet 40 device is stated to be a whole blood and plasma viscometer that tracks the meniscus of a blood sample that falls due to gravity through a capillary. While the Hevimet 40 device may be generally suitable for some whole blood or blood plasma viscosity determinations, it appears to exhibit several significant drawbacks. For example, among other things, the Hevimet 40 device appears to require the use of anti-coagulants. Moreover, this device relies on the assumption that the circulatory characteristics of the blood sample are for a period of 3 hours the same as that for the patient's circulating blood. That assumption may not be completely valid.

Notwithstanding the existence of the foregoing technology, a need remains for an apparatus and method for obtaining the viscosity of the blood of a living being in-vivo and over a range of shears and for the provision of such data in a short time span.

OBJECTS OF THE INVENTION

Accordingly, it is the general object of the present invention to provide an apparatus and methods for meeting that need.

It is a further object of this invention to provide viscosity measuring apparatus and methods for determining the viscosity of circulating blood over a range of shear rates, especially at low shear rates.

It is still yet a further object of this invention to provide an apparatus and methods for determining viscosity of the circulating blood of a living being (e.g., in-vivo blood viscosity measurement) without the need to directly measure pressure, flow and volume.

It is yet another object of this invention to provide an indication of the viscosity of the circulating blood of a living being in a short span of time.

It is yet another object of this invention to provide an apparatus and methods for measuring the viscosity of the circulating blood of a living being and with minimal invasiveness.

It is still yet another object of the present invention to provide an apparatus and methods for measuring the viscosity of the circulating blood of a living being that does not require the use of anti-coagulants, or other chemicals or biologically active materials.

It is still yet another object of the present invention to provide an apparatus and methods for measuring the absolute viscosity of a patient's blood.

It is still yet another object of the present invention to provide an apparatus and methods for measuring the effective viscosity of a patient's blood.

It is still yet another object of the present invention to provide an apparatus and method for measuring the relationship of the patient's absolute viscosity to his/her effective viscosity.

It is still yet another object of the present invention to provide an apparatus and methods for determining the propensity of a patient to form a thrombosis based on the relationship of the patient's absolute viscosity to the patient's effective viscosity.

It is still yet another object of the present invention to provide an apparatus and methods for distinguishing those patients experiencing chest pains due to a life-threatening acute vessel occlusion from those patients whose chest pains are not due to such occlusion.

It is still yet another object of the present invention to provide an apparatus and methods for a physician to determine the quantity of therapeutic drug to be administered to a patient to alleviate the occlusion.

It is still yet another object of the present invention to provide an apparatus methods for a physician to determine the short-term and the long-term efficacy of the administered therapeutic drug on the patient's condition.

It is still yet another object of the present invention to provide an apparatus and methods for showing that a change in viscosity of a patient's circulating blood is caused by any interaction in the blood due to external factors, e.g., that may be temperature-related, drug-related, time-related, etc.

It is still yet even another object of the present invention to provide an apparatus and method for measuring the viscosity of blood of a living being that does not require the blood to be exposed to atmosphere or oxygen.

It is still yet another object of the present invention to provide an apparatus and method for determining the viscosity of the circulating blood contemporaneous with the diversion of the blood into a conveying means (e.g., needle) when that means is coupled to, e.g., inserted into, the patient.

It is still yet another object of the present invention to provide an apparatus and methods for measuring the circulating blood viscosity of a living being that comprises disposable portions for maintaining a sterile environment, ease of use and repeat testing.

It is still yet another object of the present invention to provide a blood viscosity measuring apparatus and methods for determining the thixotropic point of the blood.

It is even yet another object of the present invention to provide an apparatus and methods for determining the yield stress of the circulating blood.

It is moreover another object of the present invention to provide an apparatus and methods for detecting circulating blood viscosity to evaluate the efficacy of pharmaceuticals, etc., to alter blood viscosity of the circulating blood of a living being.

It is even yet another object of this invention to provide an apparatus and methods for detecting the viscosity of the circulating blood of a patient while negating the effects of venous pressure.

It is still yet another object of this invention to provide an apparatus and method that can be used as a screening test and diagnostic tool for numerous blood pathologies.

It is even yet another object of this invention to provide an apparatus and method for enabling a cyclical viscosity management, i.e., keeping patient's CBV as steadyas possible.

It is another object of this invention to provide an apparatus and method forproviding a drug delivery amount determinant in critical care settings, i.e., MI (myocardial infarction), stroke, PVD (pulmonary vascular disease).

It is another object of this invention to provide an apparatus and method forproviding an indicator of various patient conditions, such as MI, stroke, PVD, etc., based on the patient's circulating blood viscosity.

It is another object of this invention to provide an apparatus and method that enables the manipulation of the shape of a patient's absolute and effective viscosity curves with drug administration/therapy.

It is still yet another object of this invention to provide an apparatus and method for measuring the yield stress of the blood of a living being.

SUMMARY OF THE INVENTION

These and other objects of the instant invention are achieved by providing a method for detecting interactions in the circulating blood of a living being caused by external factors (e.g., administering a drug, smoking, poor diet, etc.) by analyzing the viscosity of the living being's circulating blood.

In accordance with one aspect of the invention, the viscosity of the living being's circulating blood is determined (e.g., in real time) over a first shear rate range (e.g., $320 \text{ s}^{-1}$ to $1 \text{ s}^{31}{}^{1}$) in order to determine a first viscosity profile (absolute viscosity) and the viscosity of the living being's circulating blood is also determined over that first shear rate range in combination with a second shear rate range (e.g., $1\text{s}^{-1}$ to $0.02 \text{ s}^{-1}$) to determine a second viscosity profile (effective viscosity). The relationship between the first viscosity profile and a horizontal line is determined as well as the relationship between the first viscosity profile and the second viscosity profile. From these relationships, the interactions in the circulating blood caused by the external factors can be detected.

In accordance with still another aspect of this invention an apparatus is provided for detecting interactions in the circulating blood in a living being caused by external factors. The apparatus comprises: a lumen arranged to be coupled to the vascular system of the being; a pair of tubes having respective first ends and second ends wherein the first ends are coupled together via a capillary tube having some known parameters; a valve for controlling the flow of circulating blood from the being's vascular system to the pair of tubes wherein the valve is coupled to a second end of one of the pair of tubes and is coupled to the lumen; and an analyzer, coupled to the valve, for controlling the valve to permit the flow of blood into the pair of tubes whereupon the blood in each of the pair of tubes assumes a respective initial position with respect thereto. The analyzer also is arranged for operating the valve to isolate the pair of tubes from the being's vascular system so that the position of the blood in the pair of tubes changes. The analyzer also is arranged for monitoring the blood position change in the tubes and calculating the viscosity of the living being's blood (e.g., in real-time) over a first shear rate range (e.g., $320 \text{ s}^{-1}$ to $1 \text{ s}^{31}{}_{1}$) and a second shear rate range (e.g., $1\text{s}^{-1}$ to $0.02 \text{ s}^{-1}$) based on the blood position change and on selected known parameters of the capillary tube in order to determine a first viscosity profile (absolute viscosity) and a second viscosity profile (effective viscosity). From these relationships, the interactions in the circulating blood caused by the external factors can be detected.

In accordance with another aspect of this invention an apparatus is provided for detecting interactions in the circulating blood of a living being caused by external factors. The apparatus comprises: a lumen arranged to be coupled to the vascular system of the being and a pair of tubes having respective first ends coupled to the lumen for receiving circulating blood from the being and wherein one of the pair of tubes comprises a capillary tube having some known parameters. A valve controls the flow of circulating blood from the being's vascular system to the pair of tubes. The apparatus further comprises an analyzer, coupled to the valve, for controlling the valve to permit the flow of blood into the pair of tubes whereupon the blood in each of the pair of tubes assumes a respective initial position with respect thereto. The analyzer is also arranged for operating the valve to isolate the pair of tubes from the being's vascular system so that the position of the blood in the pair of tubes changes. The analyzer is also arranged for monitoring the blood position change in the tubes and for calculating the viscosity of the living being's blood (e.g., in real-time) over a first shear rate range (e.g., 320 s$^{-1}$ to 1 s$^{-1}$) and a second shear rate range (e.g., 1s$^{-1}$ to 0.02 s$^{-1}$) based on the blood position change and on selected known parameters of the capillary tube to determine a first viscosity profile (absolute viscosity) and a second viscosity profile (effective viscosity) for detecting the interactions in the circulating blood of a living being caused by the external factors. From these relationships, the interactions in the circulating blood caused by the external factors can be detected.

In accordance with another aspect of this invention, a method for determining the yield stress of the circulating blood of a living being is achieved by: (a) providing access to the circulating blood of the living being to form an input flow of circulating blood; (b) directing the input flow into one end of a pair of tubes coupled together via a passageway having some known parameters wherein the input flow passes through a first one of the pair of tubes, through the passageway and into a first portion of a second one of the pair of tubes in order to form respective columns in the first and second tubes; (c) isolating the respective columns from the input flow so that the position of the blood in each of the columns changes; (d) monitoring the blood position change in the respective columns of blood over time; (e) detecting a difference (e.g., ΔΔh) between the final levels of the columns; and (f) calculating the yield stress of the blood based on the difference and on selected known parameters of the passageway.

In accordance with another aspect of this invention, an apparatus is provided for determining the yield stress of the circulating blood of a living being. The apparatus comprises: a lumen arranged to be coupled to the vascular system of the being; a pair of tubes having respective first ends and second ends wherein the first ends are coupled together via a capillary tube having some known parameters; a valve for controlling the flow of circulating blood from the being's vascular system to the pair of tubes and wherein the valve is coupled to a second end of one of the pair of tubes and is coupled to the lumen; and an analyzer, coupled to the valve, for controlling the valve to permit the flow of blood into the pair of tubes whereupon the blood in each of the pair of tubes assumes a respective initial position with respect thereto. The analyzer also is arranged for operating the valve to isolate the pair of tubes from the being's vascular system so that the position of the blood in the pair of tubes changes. The analyzer is also arranged for monitoring the blood position change in the tubes over time and for detecting a difference (e.g., Δh) between the final positions of the blood in the pair of tubes. The analyzer calculates the yield stress of the circulating blood based on the difference and on selected known parameters of the capillary tube.

In accordance with another aspect of this invention, a method for determining the yield stress of the circulating blood of a living being is achieved by: (a) providing access to the circulating blood of the living being to form an input flow of circulating blood; (b) dividing the input flow of circulating blood into a first flow path and a second flow path into which respective portions of the input flow pass and wherein one of the first or second flow paths includes a passageway portion having some known parameters; (c) isolating the first and second flow paths from the input flow and coupling the first and second flow paths together so that the position of the blood in each of the flow paths changes; (d) monitoring the blood position change in the first and second flow paths over time; (e) detecting a difference (e.g., Δh) between the final positions of the blood in the first and second flow paths; and (f) calculating the yield stress of the blood based on the difference and on selected parameters of passageway portion.

In accordance with another aspect of this invention, an apparatus is provided for determining the yield stress of the circulating blood of a living being. The apparatus comprises: a lumen arranged to be coupled to the vascular system of the being; a pair of tubes having respective first ends coupled to the lumen for receipt of circulating blood from the being and wherein one of the pair of tubes comprises a capillary tube having some known parameters; a valve for controlling the flow of circulating blood from the being's vascular system to the pair of tubes; and an analyzer, coupled to the valve, for controlling the valve to permit the flow of blood into the pair of tubes whereupon the blood in each of the pair of tubes assumes a respective initial position with respect thereto. The analyzer also is arranged for operating the valve to isolate the pair of tubes from the being's vascular system and for coupling the pair of tubes together so that the position of the blood in the pair of tubes changes. The analyzer also is arranged for monitoring the blood position change in the tubes over time and for detecting a difference (e.g., Δh) between the final positions of the blood in the pair of tubes. The analyzer calculates the yield stress of the circulating blood based on the difference and on selected known parameters of the capillary tube.

In accordance with another aspect of the invention a method is provided for determining the effects of drugs, introduced into a living being, that are designed to treat a condition of the living being. The method comprises the step of analyzing the viscosity of the living being's circulating blood.

In accordance with one aspect of the invention, the viscosity of the living being's circulating blood is determined (e.g., in real time) and analyzed over a first shear rate range (e.g., 320 s$^{-1}$ to 1 s$^{31\ 1}$) in order to determine a first viscosity profile (absolute viscosity) and the viscosity of the living being's circulating blood is also determined over that first shear rate range in combination with a second shear rate range (e.g., 1s$^{-1}$ to 0.02 s$^{31\ 1}$) to determine a second viscosity profile (effective viscosity). The relationship between the first viscosity profile and a horizontal line is determined as well as the relationship between the first viscosity profile and the second viscosity profile. From these relationships, the effects of drugs designed to treat a condition of the living being can be detected.

DESCRIPTION OF THE DRAWINGS

Other objects and many of the intended advantages of this invention will be readily appreciated when the same becomes better understood by reference to the following detailed description when considered in connection with the accompanying drawings wherein.

DETAILED DESCRIPTION OF THE PREFERRED EMBODIMENTS

As stated previously, the present application is a Continuation-in-Part of Co-Pending application Ser. No. 09/439,795, filed Nov. 12, 1999, entitled DUAL RISER/ SINGLE CAPILLARY VISCOMETER, which is assigned to the same Assignee as the present invention and whose entire disclosure is incorporated by reference herein. The apparatus disclosed in application Ser. No. 09/439,795 provides the medical community the ability to observe the instantaneous circulating blood viscosity characteristic that has, up until now, not been detectable by conventional blood viscometers.

Figure 1:
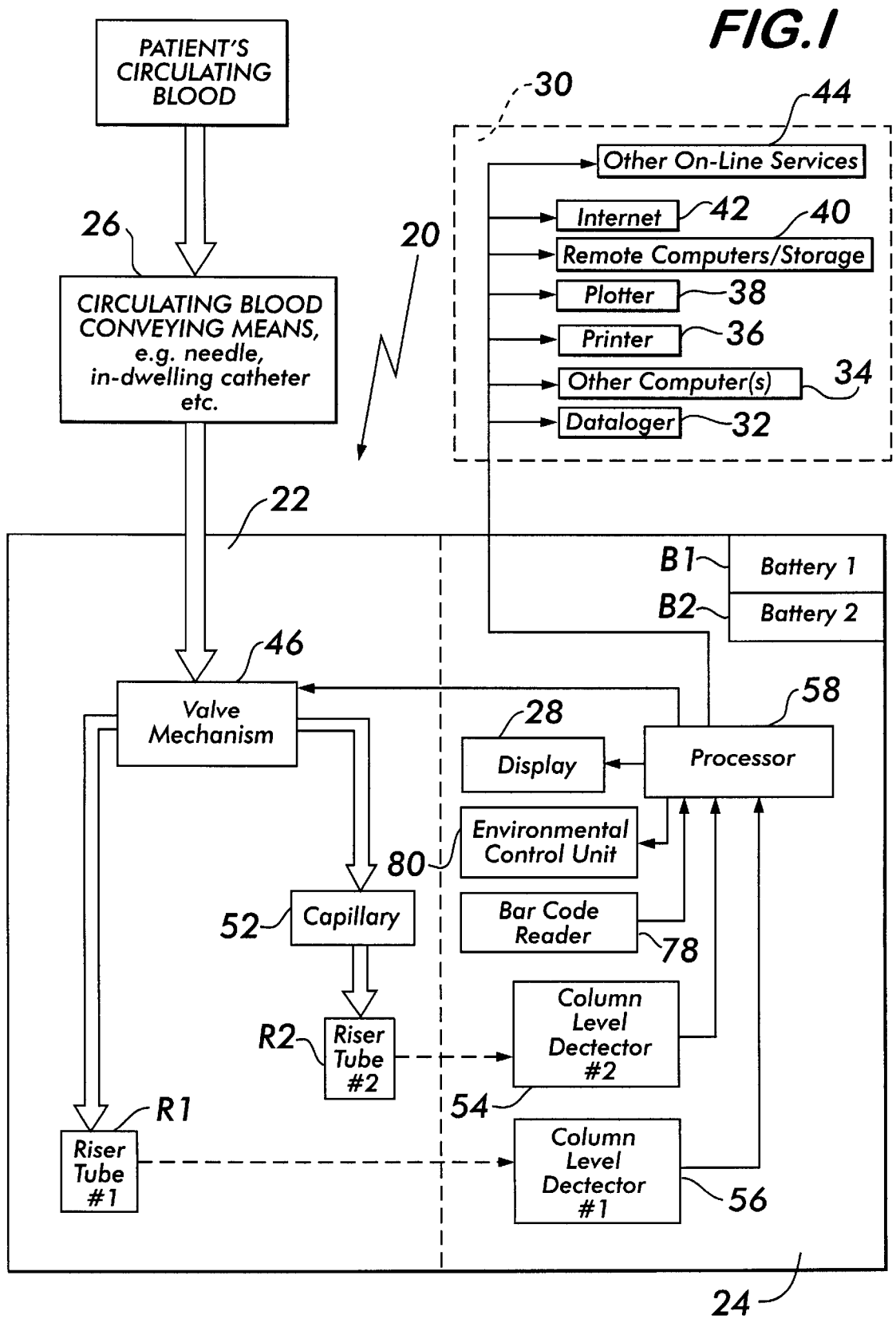
FIG. 1 is a block diagram of a dual riser/single capillary (DRSC) viscometer.

In particular, the apparatus disclosed in application Ser. No. 09/439,795 comprises a first embodiment of a dual riser/single capillary (DRSC) viscometer shown in FIGS. 1 and 2, and a second embodiment of the DRSC viscometer shown in FIGS. 3 and 4, and each of which measure the viscosity of circulating blood, including whole blood, of a living being. For purposes of the present application, either embodiment can be used to achieve the method described herein.

Basically, the DRSC viscometers 20 (FIG. 1) and 120 (FIG. 3) comprise a blood receiving means 22 and 122, respectively, and an analyzer/output portion 24. The patient is coupled to the DRSC viscometers 20/120 through a circulating blood conveying means 26, e.g., a needle, an IV needle, an in-dwelling catheter, etc., or any equivalent structure that can convey circulating blood from a patient to the DRSC viscometers 20/120. The analyzer/output portion 24 includes a microprocessor 58 that, among other things, calculates the circulating blood viscosity based on the information that it receives from the blood receiving means 22/122. A display 28 is also provided for presenting the viscosity information, as well as other information to the operator. The analyzer/output portion 24 may also provide this information to other suitable output means 30, such as a datalogger 32, other computer(s) 34, a printer 36, a plotter 38, remote computers/storage 40, to the Internet 42 or to other on-line services 44.

Figure 2:
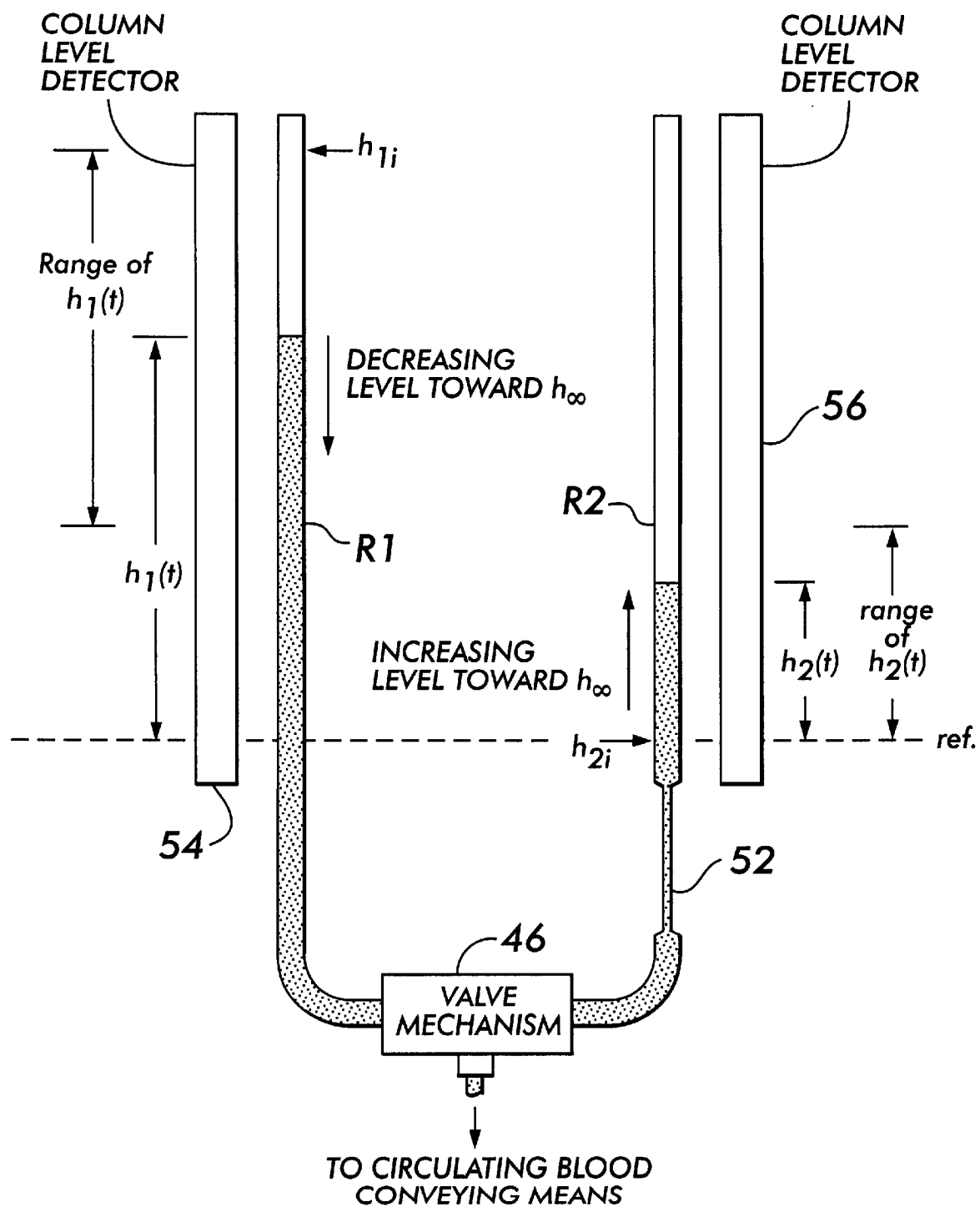
FIG. 2 is a functional diagram of the first embodiment of the DRSC viscometer during the viscosity test run.
Figure 3:
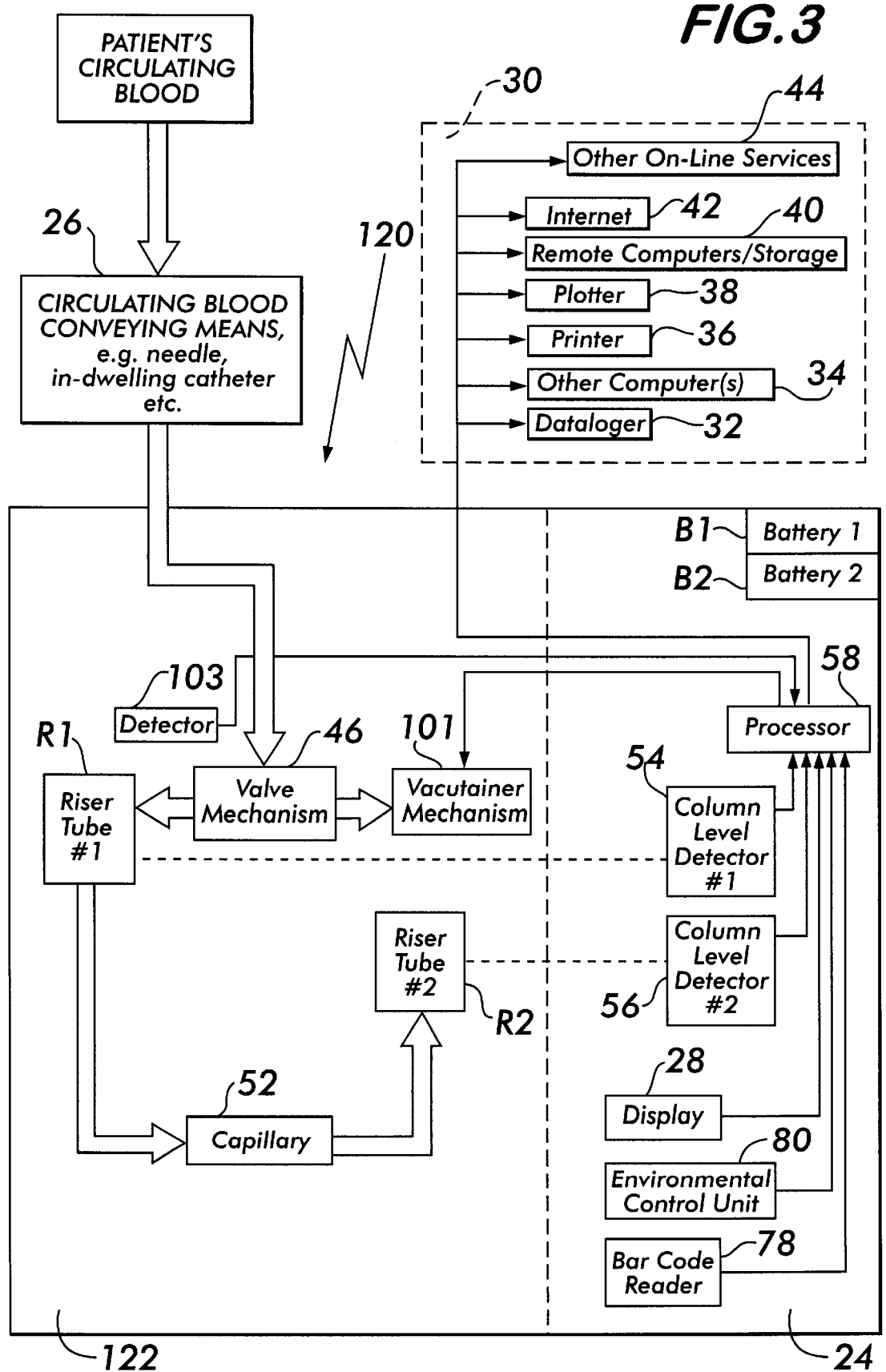
FIG. 3 is a block diagram of another DRSC viscometer.
Figure 4:
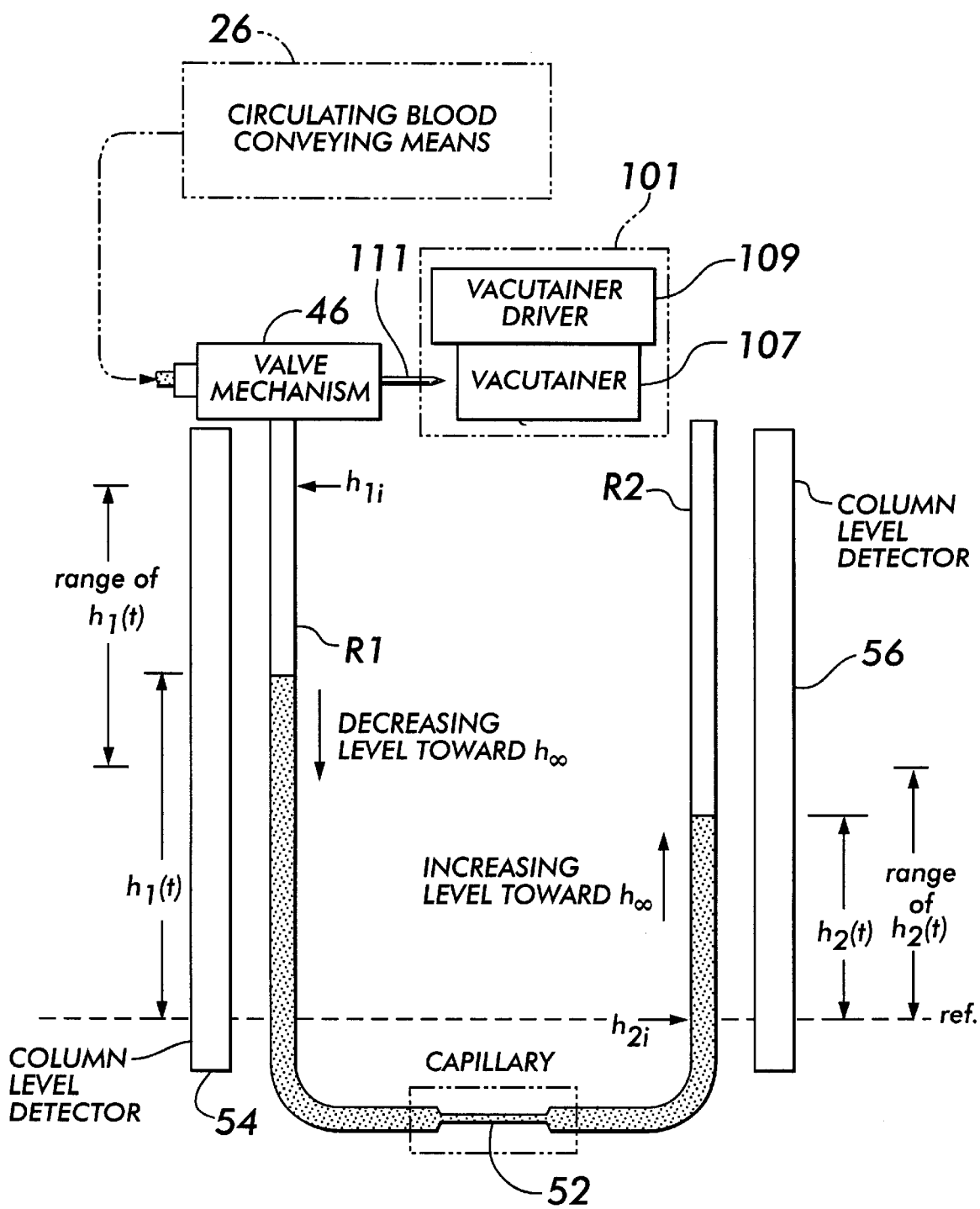
FIG. 4 is a functional diagram of the second embodiment DRSC viscometer during the viscosity test run.

The blood receiving means 22/122 basically comprises a valve mechanism 46 coupled between a first riser tube R1 and a second riser tube R2 (FIGS. 1–2), or coupled to one end of one of the riser tubes (FIGS. 3–4), for controlling the input circulating blood flow into the DRSC viscometers 20/120. In addition, a capillary tube 52 of known dimensions is coupled to one of the riser tubes (e.g., as shown in FIG. 2), or is coupled between the riser tubes (e.g., as shown in FIG. 4). In general, the valve mechanism 46 in both embodiments establishes a first initial position, $h_{1i}$, of a column of blood ($h_1$) in one of the riser tubes (e.g., R1) and a second initial position, $h_{2i}$, of another column of blood ($h_2$) in the other of the riser tubes (e.g., R2). The valve mechanism 46 then isolates these columns of blood from the input circulating blood flow, resulting in the oppositely-moving columns of blood away from their initial positions as shown in FIGS. 2 and 4. Just prior to this isolation and during the movement of the columns of blood, each column of blood is monitored by a respective column level detector 54 and 56 which send their data to the microprocessor 58. As a result, the column level detectors 54/56 collect data ($h_1(t)$ and $h_2(t)$) regarding the movement of these respective columns of blood, which can also be plotted (FIG. 5) and then displayed on the display screen 28.

Based on the above discussion, the method of the present invention is now discussed; the details of the other components depicted in FIGS. 1–4 are discussed in application Ser. No. 09/439,795, and are not repeated here.

As discussed above, the concept of viscosity determination using the DRSC viscometers 20/120 is to monitor the change in height of two, oppositely-moving, columns of blood from the circulating blood of a patient and given the dimensions of a capillary through which one of the columns of blood must flow.

As stated in application Ser. No. 09/439,795, there are a plurality of mathematical models that can be used as curve fitting models for the data obtained from the viscometers 20 and 120, such as a power law model, a Casson model, a Carreau model, a Herschel-Bulkley model, a Powell-Eyring model, a Cross model, Carreau-Yasuda model. It is within the broadest scope of this invention to include all of these models. The following discussion utilizes a power law model and is used by way of example only and not by way of limitation. Thus, one skilled in the art could substitute any of the above curve fitting models for the exemplary power law model discussed below.

In particular, for non-Newtonian fluids, as is blood, the viscosity varies with shear rate, however, Hagen-Poiseuille flow within the capillary still holds for steady or quasi-steady laminar flow. For a fluid that is well-correlated with a non-Newtonian power law viscosity model, the capillary pressure drop and flow rate are related as follows:

$$\Delta P_c = \frac{4kL_c|\dot{\gamma}|^n}{\phi_c} = \frac{4kL_c}{\phi_c}\left|\left(\frac{3n+1}{n}\right)8\frac{Q}{\pi\phi_c^3}\right|^n \tag{1}$$

where the shear rate, $\dot{\gamma}$ is related to the capillary flow rate by:

$$\dot{\gamma} = \left(\frac{3n+1}{n}\right)8\frac{Q}{\pi\phi_c^3} \tag{2}$$

where the power viscosity is defined as:

$$\mu = k|\dot{\gamma}|^{n-1} \tag{3}$$

and where
- $\Delta P_c$=capillary tube pressure drop (Pa)
- $L_c$=length of capillary tube (m)
- Q=volumetric flow rate (m³/s)
- k=consistency index (a constant used in capillary viscometry)—that is determined
- n=power law index (another constant used in capillary viscometry)—that is determined
- $\phi_c$=inside diameter of capillary tube (m)
- $\mu$=fluid viscosity (centipoise, CP)
- $\dot{\gamma}$=shear rate (s⁻¹)

Since blood, a non-Newtonian fluid, is well-characterized with a power law viscosity model, Equation (1) can be re-written as:

$$\rho g(h_1(t) - h_2(t)) = \frac{4kL_c}{\phi_c}\left\{2\left(\frac{3n+1}{n}\right)\cdot\left(\frac{\phi_r^2}{\phi_c^3}\right)\left|\frac{dh}{dt}\right|\right\}^n + \rho g \Delta h \quad (4)$$

where
- $\rho$=blood fluid density;
- g=gravitational constant;
- $h_1(t)$=instantaneous height of the column of blood in riser R1
- $h_2(t)$=instantaneous height of the column of blood in riser R2
- $\phi_r$=inside diameter of riser tube and where $\phi_c \lll \phi_r$
- $\Delta h$=an offset due to yield stress of the blood.

It should be noted that the length of the capillary tube $L_c$ is assumed large such that any friction losses in the riser tubes R1 and R2 and connecting fluid components can be ignored. In addition, the diameter of the riser tubes R1 and R2 are equal.

By integrating both sides of Equation (4) with respect to time yields:

$$h_1(t) - h_2(t) - \Delta h = -\left\{\left(\frac{n-1}{n}\right)\alpha t + (\Delta h - h_0)^{\frac{n-1}{n}}\right\}^{\frac{n}{n-1}} \quad (5)$$

where
- $h_0 = h_1(t) - h_2(t)$ at t=0; and $$\alpha = -\frac{1}{2}\left(\frac{4kL_c}{\rho g d_c}\right)^n \left(\frac{n}{3n+1}\right)\left(\frac{\phi_c^3}{\phi_r^2}\right) \quad (6)$$

Figure 5:
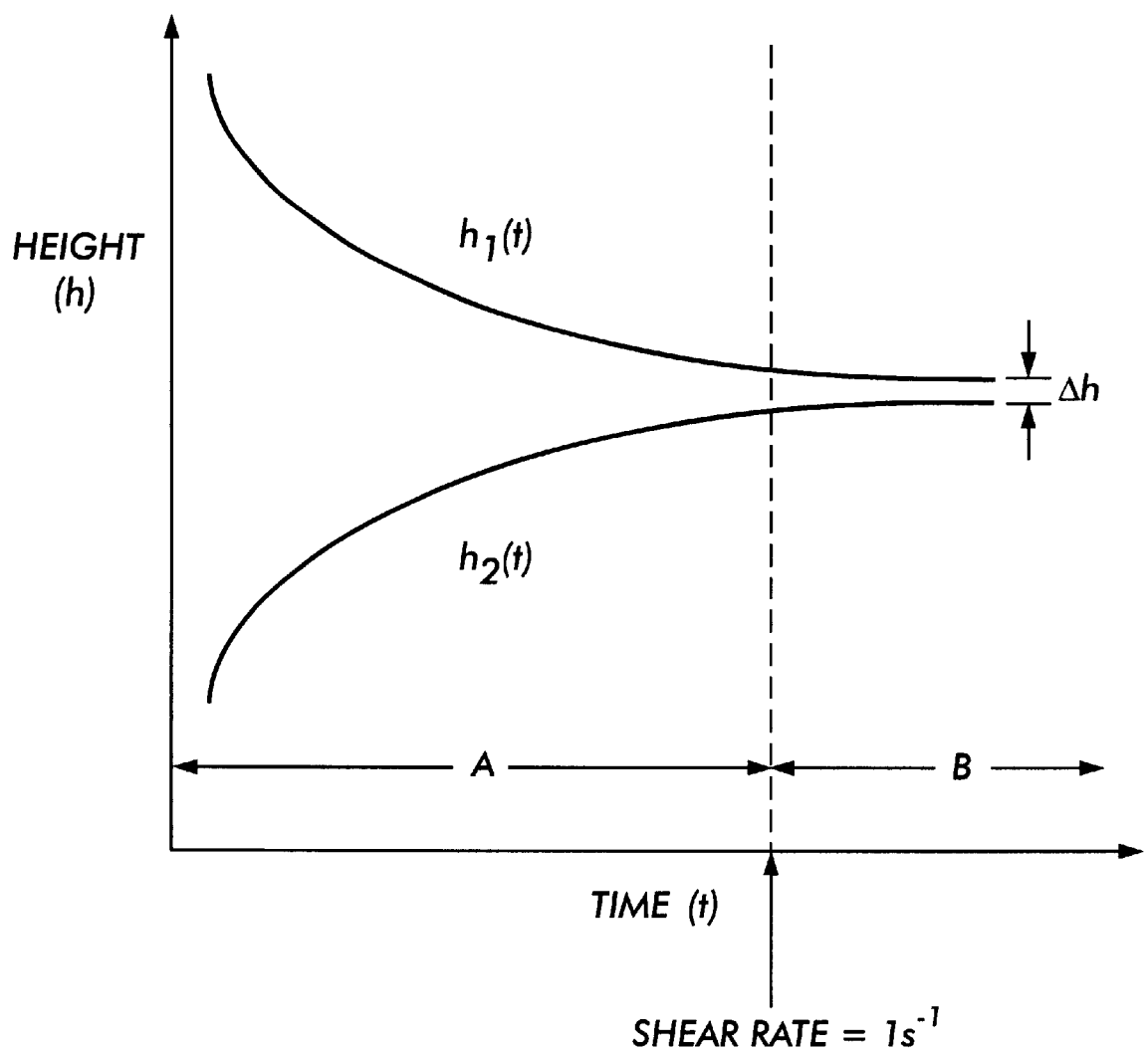
FIG. 5 depicts a graphical representation of the respective columns of fluid in the riser tubes of either the first or second embodiment of the DRSC viscometer during the viscosity test run.

In order to determine the viscosity, it is necessary to determine the values for k and n using curve fitting based on the test run data. In particular, the following procedure is used:
1) Conduct a test run and obtain all $h_1(t)$ and $h_2(t)$ data;
2) Fit curves through the data to obtain symbolic expressions for $h_1(t)$ and $h_2(t)$;
3) Determine all $h_1(t)-h_2(t)$ data, as well as $\Delta h$; FIG. 5 depicts a graphical representation of $h_1(t)$ and $h_2(t)$, as well as $\Delta h$.
4) Assume values for the power law parameters k and n;
5) Calculate the following error values for all data points:

$$Error = \left|(h_1(t) - h_2(t) - \Delta h) - \left\{\left(\frac{n-1}{n}\right)\alpha t + (\Delta h - h_0)^{\frac{n-1}{n}}\right\}^{\frac{n}{n-1}}\right| \quad (7)$$

6) Sum the error values for all data points;
7) Iterate to determine the values of k and n that minimize the error sum; and
8) Use the determined k and n values in Equations (2) and (3) to calculate viscosity.

It should be reiterated that the steps involving the parameters k and n are only necessary where a power law model is used. If another curve fitting model (listed above) were used, the steps involving k and n would be omitted.

Using the above sequence, the method for obtaining absolute viscosity and effective viscosity is now discussed.

A non-Newtonian fluid is one that does not conform to Newton's laws of fluids. At a given point, the rate of shear in a Newtonian fluid (under isothermal conditions) is linearly proportional to the corresponding stress such that Newtonian viscosity is independent of shear rates. A non-Newtonian fluid does not meet this requirement under all circumstances; many of these non-Newtonian fluids demonstrate different properties under different flow conditions. Furthermore, some non-Newtonian fluids, e.g., blood, vary with both shear rate and time. Using either viscometer 20 or 120, the viscosity of such non-Newtonian fluids can be measured.

Blood should be considered a time dependent, non-Newtonian fluid, i.e., the viscosity of the blood is dependent on temperature, shear rate and time. Non-Newtonian biological fluids, such as blood, demonstrate irreversible changes in chemistry that permanently alter the viscosity profile (e.g., clotting, coagulation, etc.). These fluids also demonstrate different properties under different flow conditions, Therefore, the measurement of the viscosity of blood must take into account the irreversible changes that occur overtime. For the purposes of this disclosure, the viscosity of blood during the time before it undergoes any irreversible changes is referred to as "absolute viscosity; and the viscosity overtime including such irreversible changes is referred to as "effective viscosity."

As discussed previously, as time passes, the shear rate of the blood in the viscometers 20/120 decreases. In most cases, a shear rate of 1s⁻¹ reached within approximately two minutes, an accepted time period during which minimal, if any, changes occur to blood. The viscometers 20/120 also mimic in-vivo conditions (through use of thermal control and biocompatible coatings) to minimize the potential of irreversible changes within the first two minutes. As the instrument makes continuous viscosity measurements over a time period of approximately four minutes, 12,000 data points are collected and plotted on a height versus time scale. The data is curve-fitted (using one of many possible mathematical models discussed previously) and the resulting curve is used to derive viscosity, as previously described.

Analysis of the viscosity over the entire range of shear is divided into two major regions A and B (FIG. 5), wherein region A represents a first shear rate range of approximately 320 s⁻¹ down to approximately 1 s⁻¹; region B represents a second shear rate range below 1 s⁻¹ toward zero shear rate. During region A, there is nothing significant occurring with regard to the clotting factor. By analyzing the first shear rate range (which may vary slightly with patient) of approximately 320s⁻¹ to 1s⁻¹, standard non-Newtonian fluid viscosity measurements for the blood are derived. Blood viscosity calculated in region A is plotted in FIG. 6 using a log $\mu$ versus log $\dot{\gamma}$ (s⁻¹). The viscosity calculated in region A is the "absolute" viscosity because as a non-Newtonian fluid (not including any biophysical or chemical interactions), the blood has an absolute viscosity profile.

When the shear rates in the second shear rate range are encountered (<1 s⁻¹), i.e., region B, where clotting factors begin appearing, the entire data set (i.e., region A data+ region B data, which usually extends to a shear rate of approximately $0.02s^{-1}$) is analyzed over the full four-minute test. It is in the latter two minutes of the test wherein possibly irreversible (via physical force) changes occur in the blood. This causes a more significant increase in apparent viscosity due to clotting, coagulation or other biophysical interaction. Blood viscosity calculated during the second shear rate range portion of the viscosity test is plotted in FIG. 6 again using the log $\mu$ versus log $\dot{\gamma}$ ($s^{-1}$) scale and is indicated by the plot labeled "A+B". As can be seen, there is an apparent increase in total blood viscosity profile, which is hereinafter referred to as "effective viscosity." The use of the term "effective viscosity" is such because it is the entire shear rate range which best represents the cardiac cycle.

There is no difference in the mathematics used to derive absolute and effective viscosity. Both are the same curve fitting operation: one on one data set, one on another. The shift in angle of the profile is due to the things mentioned above. By analyzing the data twice, a representative viscosity profile of the patient's blood (1) acting as simply a non-Newtonian fluid and (2) acting as a biological fluid that undergoes a form of irreversible change during the second shear rate range is obtained. This method enables the medical community to clearly and quickly show that different patients have different profiles. This analysis is done continuously, without modifying the environmental parameters (e.g., no clotting agent is administered to the patient) and closely replicates the shear rates experienced by the blood during the cardiac cycle.

Figure 6:
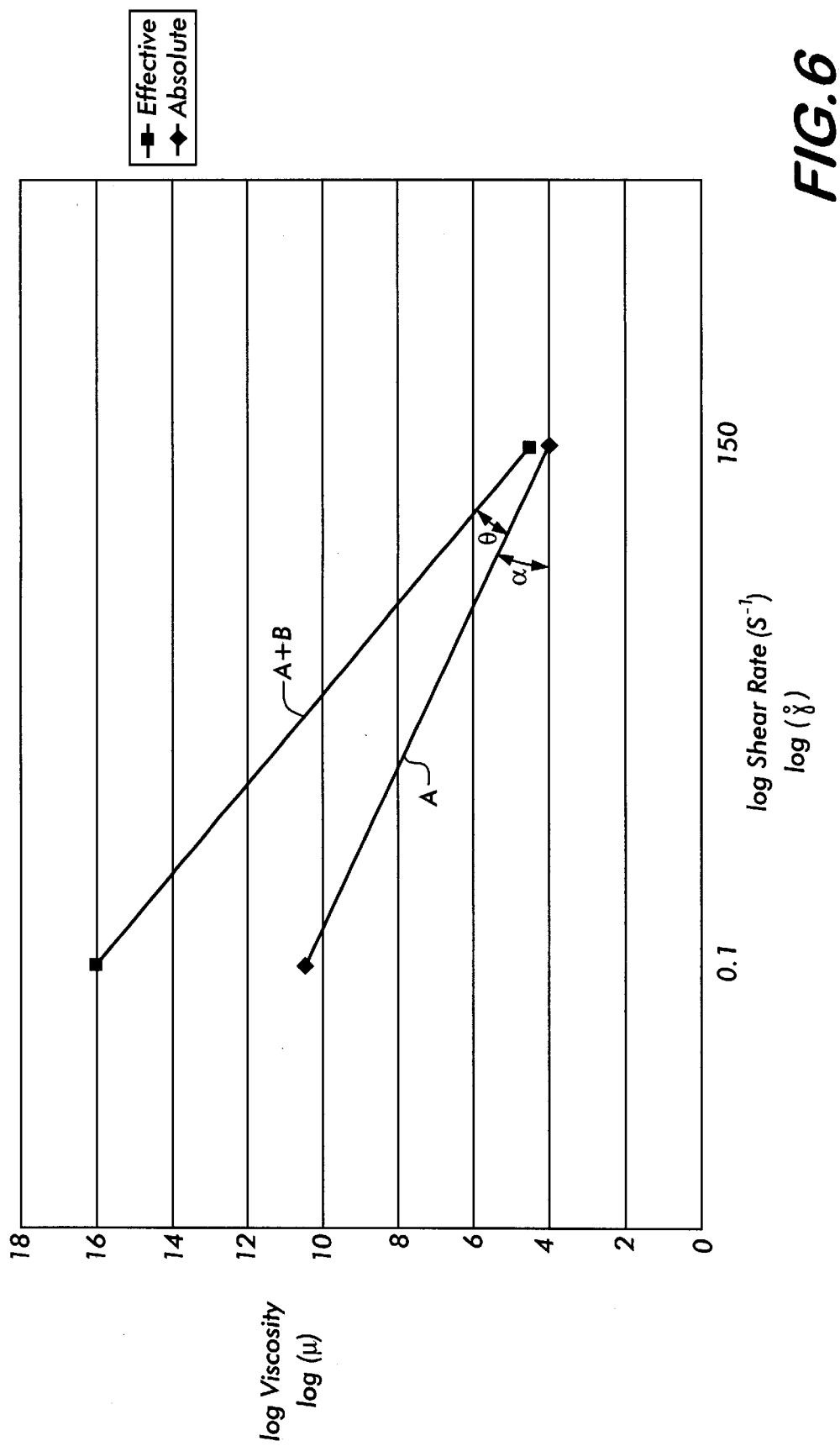
FIG. 6 depicts a graphical representation of the absolute viscosity versus the effective viscosity.

In comparing the two plots shown in FIG. 6, it is apparent that there is a total shift, i.e., the effective viscosity is not only pivoted away from the absolute viscosity but it is also shifted; alternatively, for example, in some cases, the effective viscosity may only be pivoted away from the absolute viscosity but not shifted.

The angle $\alpha$ that the absolute viscosity profile makes with the horizontal axis can be used as a simple indicator for viscosity, and the angle $\theta$ that the effective viscosity profile makes with the absolute viscosity profile, can be used as a more advanced indicator for other blood parameters. The ideal condition of the blood is to produce a data set wherein $\alpha$ is minimized and where $\theta=0°$. A poor condition exists where $\alpha$ is not minimized and $\theta>0°$.

For example, if $\alpha$ is minimized and $\theta=0°$, that is indicative of an individual with low hematocrit and low potential of thrombosis. If $\alpha$ is not minimized and $\theta>0°$, that indicates an individual with high hematocrit (or other influence such as high triglycerides or cholesterol) and high potential of thrombosis, clotting, low deformability, etc.

It should also be understood that the angle formed between the horizontal axis and the effective viscosity can also be used as an indicator for other blood parameters.

In addition to the above method, platelet aggregation (PA) and red blood cell deformability (RBCD) measurements can be obtained after the viscosity test run is completed by tilting the dual riser/single capillary configuration, as is discussed in detail below.

Figure 7:
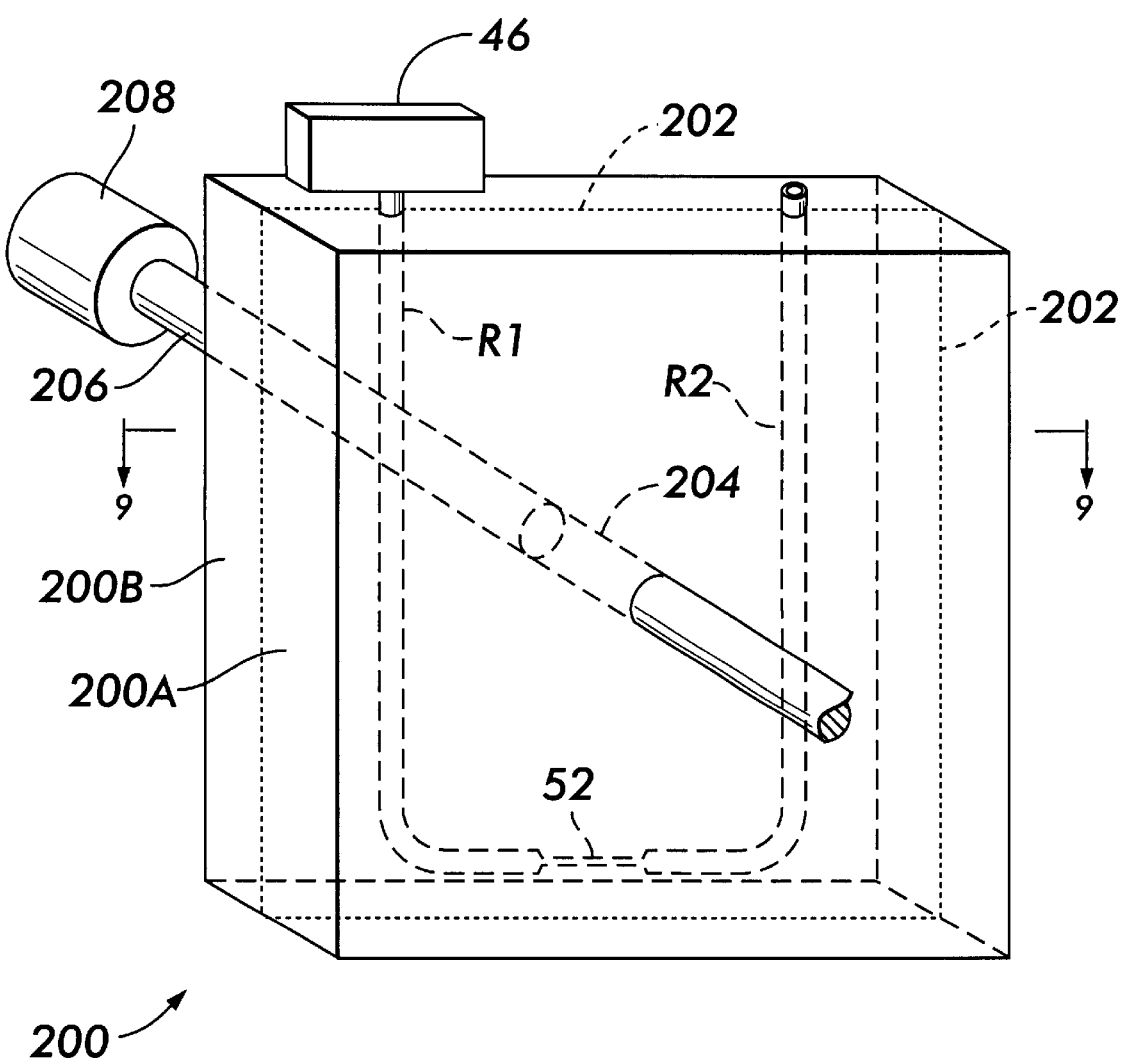
FIG. 7 depicts a dual riser tube/single capillary configuration disposed inside a pivoting transparent cartridge.
Figure 9:
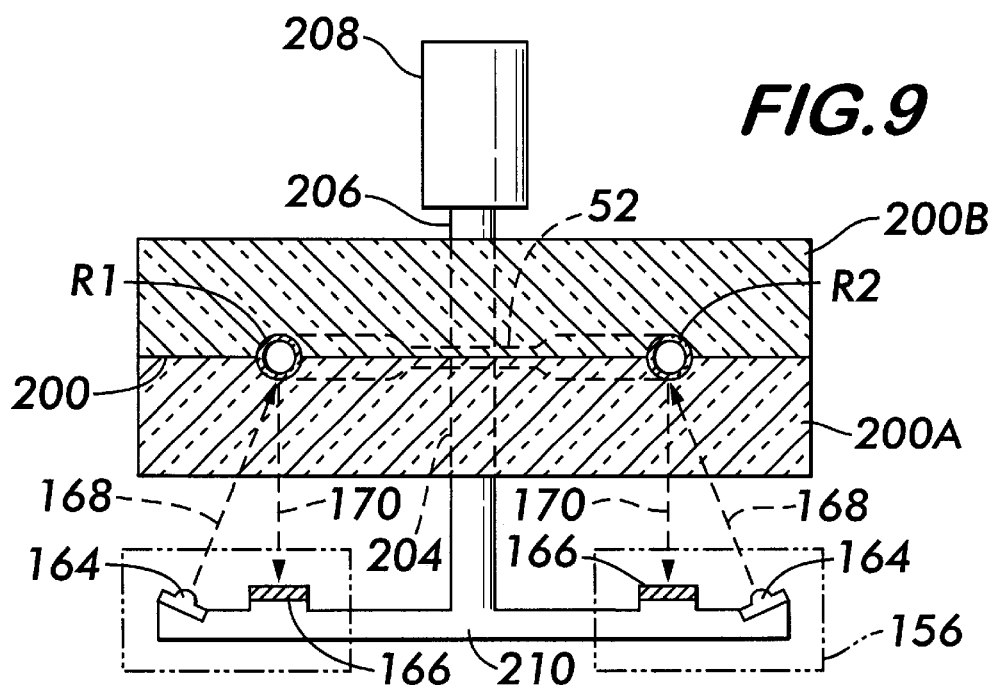
FIG. 9 is a cross-sectional view of the transparent cartridge taken along line 9—9 of FIG. 7 showing the column level detector operation.

In particular, as shown in FIGS. 7 and 9, the riser tubes R1 and R2 and the capillary tube 52 of the viscometer 120 form a portion of a transparent cartridge 200. The cartridge 200 comprises portions 200A and 200B, each of which comprises one half of the riser tube R1–R2/capillary 52 configuration. These portions 200A/200B are fixedly secured together (e.g., ultrasonic weld 202). The transparent cartridge 200 further comprises an opening 204 through which a shaft 206 passes. One end of the shaft 206 is coupled to a rotating drive mechanism 208 (e.g., a gear mechanism, a step motor, etc.) that is controlled by the processor 58, for pivoting the transparent cartridge clockwise or counter-clockwise within the housing (not shown; see application Ser. No. 09/439,795, FIG. 14, which depicts the housing 60) of the blood receiving means 122. As shown in FIG. 9, the other end of the shaft 206 comprises a "T-member" 210 for supporting respective column level detectors 154 and 156. Each column level detector 154/156 comprises an LED array 164 and a CCD 166. During operation, each LED array 164 emits light rays 168. If blood is present in a respective riser tube, the light rays 168 are reflected and impinge on the CCDs 166, as shown by the reflections 170; if, on the other hand, no blood is present in the risers, the light rays 168 simply pass through the riser tubes R1 or R2 with no reflections being detected by the CCDs 166. Thus, the column level detectors 154/156 are in fixed position with respect to their corresponding riser tubes at all times.

Figure 8A:
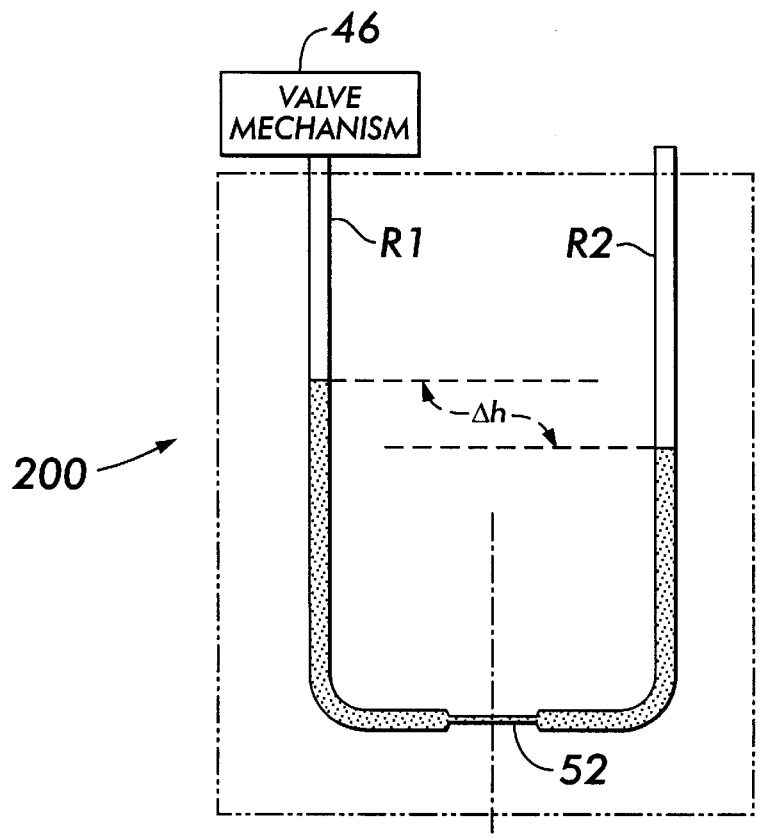
FIG. 8A is a functional diagram of the transparent cartridge at the end of the viscosity test run.

FIG. 8A depicts the state of the columns of blood in each of the riser tubes R1 and R2 at the end of the viscosity test run, namely, the levels of the two columns are separated by Δh. The cartridge 200 is then pivoted in either a clockwise or a counterclockwise direction.

Figure 8B:
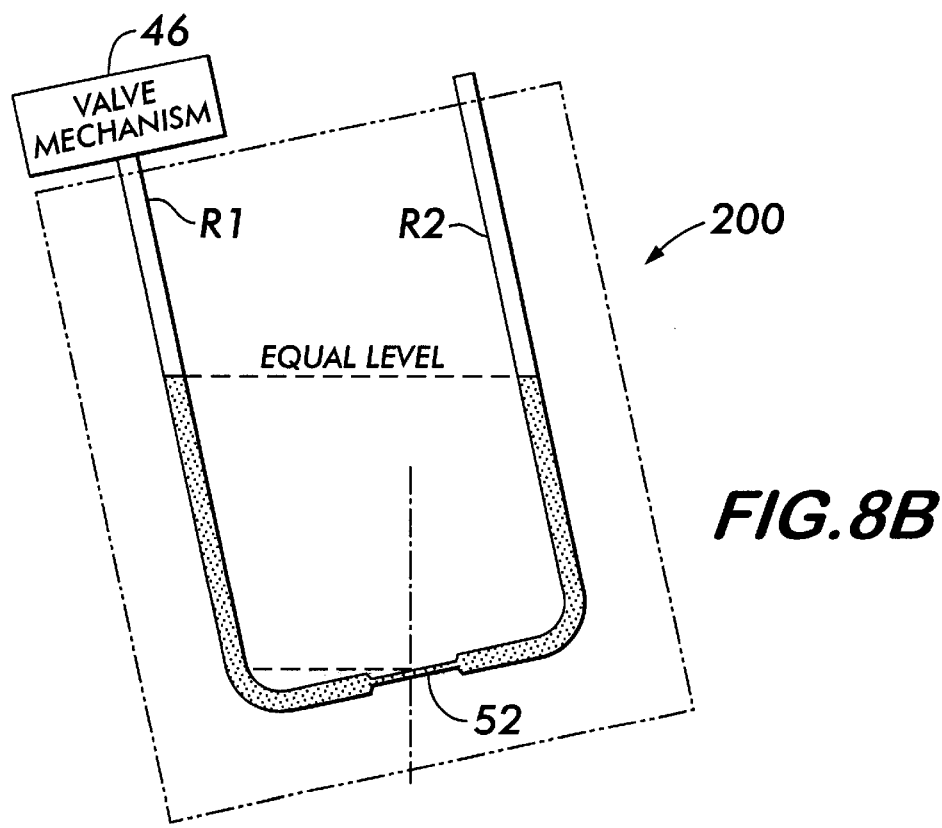
FIG. 8B is a functional diagram of the transparent cartridge after it has been pivoted in a counterclockwise direction.

FIG. 8B depicts pivoting of the cartridge 200 in a counterclockwise direction. This action causes an added force on the right side of the dual riser/single capillary configuration, thus pushing more blood through the capillary tube 52, as blood in riser tube R2 moves slightly downward and the blood in riser tube R1 moves slightly upward. By monitoring the change in blood column levels of both riser tubes R1 and R2 during this pivoting action via column level detectors 154/156, both RBCD and PA can be measured. Ideally, if clotting is minimal, the levels of the two columns of blood will come to an equal level, as shown in FIG. 8B; on the other hand, if clotting/coagulation occurs, the two levels will remain separated even in the pivoted orientation.

Figure 8C:
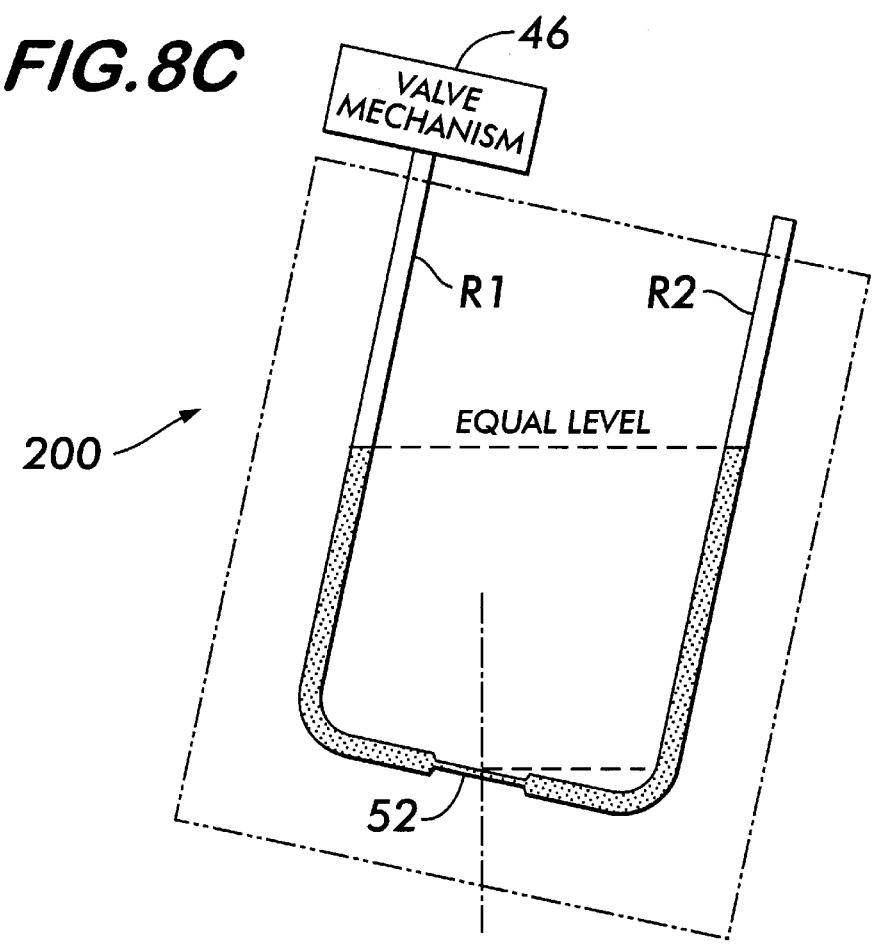
FIG. 8C is a functional diagram of the transparent cartridge after it has been pivoted in a clockwise.

FIG. 8C depicts pivoting of the cartridge 200 in a clockwise direction. This action places a force on the left side of the dual riser/single capillary configuration, thus pushing blood back through the capillary in the opposite direction, as blood in riser tube R2 moves slightly upward and the blood in riser tube R1 moves slightly downward. By monitoring the change in blood column levels of both riser tubes R1 and R2 during this pivoting action via column level detectors 154/156, both RBCD and PA can be measured. Ideally, if clotting is minimal, the levels of the two columns of blood will come to an equal level, as shown in FIG. 8C; on the other hand, if clotting/coagulation occurs, the two levels will remain separated even in the pivoted orientation.

It should be understood that the measurement of the position of each riser tube, namely, $h_1$ and $h_2$, vs. time is used to determine both RBCD and PA.

The transparent cartridge 200 is preferably a disposable element that is discarded after each viscosity test run and a new cartridge 200 is then inserted. Although not shown, the environmental control unit 80 that maintains the temperature of the transparent cartridge 200 at the patient's current body temperature may comprise a silicon heating pad that is in continuous contact with the cartridge 200 throughout the viscosity test run, as well as during the pivoting steps.

Thus, using the above apparatus and methods, it can be shown that a change in viscosity of a patient's circulating blood is caused by any interaction in the blood due to external factors, e.g., that may be temperature-related, drug-related, time-related, etc. For example, the effects of heavy smoking by a patient will be reflected in his/her absolute and effective viscosity profiles and their relationship to each other. Similarly, the effects of fatty foods being eaten by a patient will be reflected in his/her absolute and effective viscosity profiles and their relationship to each other.

As another example of the applications of the present apparatus and method is that one of the problems encountered in everyday emergency rooms is differentiating whether a patient who comes in with chest pains, or symptoms that may mimic a stroke, have actually had an acute occlusion of a vessel leading to these organs. Measuring effective viscosity in relation to absolute viscosity determines the propensity of a patient to form a thrombosis, i.e., this measurement eliminates or excludes those patients who have not had an acute occlusion from those patients who have. Thus, this eliminates the need for expensive, time-consuming procedures to determine whether they, in fact, have had a life-threatening occlusive event.

Furthermore, use of this apparatus and methods allows the physician to determine the quantity of therapeutic drug to be given and to evaluate its short-term and long-term efficacy, thus mediating the therapeutic agents and their effectiveness.

It should also be understood that, as with the embodiments disclosed in application Ser. No. 09/439,795, any means or method for detecting the movement of the columns of blood in the riser tubes R1 and R2 is within the scope of this application. Thus, changes in weight, pressure, volume, mass, etc. of the columns can be detected rather than just the column levels.

In addition, the yield stress of the blood of a living being can now be determined mathematically from the DRSC viscometers 20 and 120. Yield stress is basically defined as the shear stress below which a fluid cannot move. Alternatively, yield stress can also be defined as the shear stress that a stationary fluid must overcome to become mobile. For example, with regard to blood, there are cohesive forces among red blood cells (RBC) in plasma. In order for the blood to move, the cohesive forces among the RBCs must be broken before any fluid element begins to move. The force required to break these cohesive forces is generally termed "yield stress." In general, yield stress is the force between suspended particles in a solvent. Therefore, if there are no suspended particles, there is no yield stress. For example, mineral oil, water, glycerin, etc. do not experience yield stress whereas blood, grease, ketchup, paint, engine oil (which contains silicon particles to improve high temperature thickness), etc. do experience yield stress.

In particular, the yield stress, $\tau_0$, is defined as $$\tau_0 = \frac{\rho g \Delta h}{\pi \phi_C L_C},$$

where
 $\rho$=blood fluid density;
 g=gravitational constant;
 $\Delta h$=an offset due to yield stress of the blood;
 $\phi_c$=inside diameter of the capillary tube; and
 $L_c$=length of the capillary tube.
Since $\Delta h$ is determined using the DRSC viscometers 20/120 and since $\phi_c$ and $L_c$ are known, the yield stress, $\tau_0$, of the living being's blood can be calculated.

It should also be understood that a Casson model or a Herschel-Bulkley model can be used in determining yield stress, $\tau_0$.

Without further elaboration, the foregoing will so fully illustrate our invention and others may, by applying current or future knowledge, readily adapt the same for use under various conditions of service.

We claim:

1. A method for detecting interactions in the circulating blood of a living being caused by external factors by analyzing the viscosity of the living being's circulating blood and wherein said step of analyzing the viscosity of the living being's circulating blood comprises:
    (a) determining the viscosity of the living being's circulating blood over a first shear rate range to determine a first viscosity profile; and
    (b) determining the viscosity of the living being's blood over the first shear rate range and a second shear rate range to determine a second viscosity profile.

2. The method of claim 1 wherein said steps (a) and (b) are conducted in real time.

3. The method of claim 2 further comprising the step of determining a relationship between said first viscosity profile and a horizontal line.

4. The method of claim 3 further comprising the step of determining a relationship between said first viscosity profile and said second viscosity profile.

5. The method of claim 3 wherein said step of determining a relationship between said first viscosity profile and a horizontal line comprises the steps of:
    (a) plotting the logarithm of said first viscosity profile versus the logarithm of shear rate; and
    (b) determining a first angle formed between said first viscosity profile and said horizontal line.

6. The method of claim 5 wherein step of determining a relationship between said first viscosity profile and said second viscosity profile further comprises the steps of:
    (a) plotting the logarithm of said second viscosity profile versus the logarithm of shear rate; and
    (b) determining a second angle formed between said first viscosity profile and said second viscosity profile.

7. The method of claim 2 wherein said first shear rate range is approximately 320 $s^{-1}$ to 1 $s^{-1}$.

8. The method of claim 2 wherein said second shear rate range is approximately 1$s^{-1}$ to 0.02 $s^{-1}$.

9. The method of claim 6 further comprising the step of determining that the living being has low hematocrit and low potential of thrombosis when said first is minimized and said second angle is approximately zero degrees.

10. The method of claim 6 further comprising the step of determining that the living being has high hematocrit and high potential of thrombosis when said first angle is not minimized and said second angle is greater than zero degrees.

11. The method of claim 6 further comprising the step of determining that the living being has low triglycerides and low potential of thrombosis when said first angle is minimized and said second angle is approximately zero degrees.

12. The method of claim 6 further comprising the step of determining that the living being has high triglycerides and high potential of thrombosis when said first angle is not minimized and said second angle is greater than zero degrees.

13. The method of claim 6 further comprising the step of determining that the living being has low cholesterol and low potential of thrombosis when said first angle is minimized and said second angle is approximately zero degrees.

14. The method of claim 6 further comprising the step of determining that the living being has high cholesterol and high potential of thrombosis when said first angle is not minimized and said second angle is greater than zero degrees.

15. A method for detecting interactions in the circulating blood of a living being caused by external factors by analyzing the viscosity of the living being's circulating blood and wherein said step of analyzing the viscosity of the living being's circulating blood comprises the steps of:

(a) providing access to the circulating blood of the living being to form an input flow of circulating blood;

(b) directing said input flow into one end of a pair of tubes coupled together via a passageway having some known parameters, said input flow passing through a first one of said pair of tubes, through said passageway and into a first portion of a second one of said pair of tubes in order to form respective columns in said first and second tubes;

(c) isolating said respective columns from said input flow so that the position of the blood in each of said columns changes;

(d) monitoring the blood position change in said respective columns of blood over time; and (e) calculating the viscosity of the living being's circulating blood over a first shear rate range based on said blood position change and on selected known parameters of said passageway to determine a first viscosity profile.

16. The method of claim 15 further comprising the step of calculating the viscosity of the living being's circulating blood over said first shear rate range and a second shear rate range based on said blood position change and on said selected known parameters of said passageway to determine a second viscosity profile.

17. The method of claim 16 wherein said step of calculating the viscosity of the living being's circulating blood over said first shear rate range and a second shear rate range are conducted in real time.

18. The method of claim 17 further comprising the step of determining a relationship between said first viscosity profile and a horizontal line.

19. The method of claim 18 further comprising the step of determining a relationship between said first viscosity profile and said second viscosity profile.

20. The method of claim 18 wherein said step of determining a relationship between said first viscosity profile and a horizontal line comprises the steps of:

(a) plotting the logarithm of said first viscosity profile versus the logarithm of shear rate; and (b) determining a first angle formed between said first viscosity profile and said horizontal line.

21. The method of claim 20 wherein step of determining a relationship between said first viscosity profile and said second viscosity profile further comprises the steps of:

(a) plotting the logarithm of said second viscosity profile versus the logarithm of shear rate; and (b) determining a second angle formed between said first viscosity profile and said second viscosity profile.

22. The method of claim 17 wherein said first shear rate range is approximately 320 $s^{-1}$ to 1 $s^{-1}$.

23. The method of claim 17 wherein said second shear rate range is approximately 1$s^{-1}$ to 0.02 $s^{-1}$.

24. The method of claim 21 further comprising the step of determining that the living being has low hematocrit and low potential of thrombosis when said first angle is minimized and said second angle is approximately zero degrees.

25. The method of claim 21 further comprising the step of determining that the living being has high hematocrit and high potential of thrombosis when said first angle is not minimized and said second angle is greater than zero degrees.

26. The method of claim 21 further comprising the step of determining that the living being has low triglycerides and low potential of thrombosis when said first angle is minimized and said second angle is approximately zero degrees.

27. The method of claim 21 further comprising the step of determining that the living being has high triglycerides and high potential of thrombosis when said first angle is not minimized and said second angle is greater than zero degrees.

28. The method of claim 21 further comprising the step of determining that the living being has low cholesterol and low potential of thrombosis when said first angle is minimized and said second angle is approximately zero degrees.

29. The method of claim 21 further comprising the step of determining that the living being has high cholesterol and high potential of thrombosis when said first angle is not minimized and said second angle is greater than zero degrees.

30. The method of claim 17 wherein said respective blood columns have respective level positions following said step of monitoring the blood position change over time, said method further comprising the steps of:

(a) pivoting said respective columns of blood to a first position; and (b) monitoring said respective columns for any further blood position change away from said respective level positions over time.

31. The method of claim 30 wherein said step of pivoting said respective columns comprises pivoting said columns in a clockwise direction away from a vertical position towards said first position.

32. The method of claim 30 wherein said step of pivoting said respective columns comprises pivoting said columns in a counterclockwise direction away from a vertical position towards said first position.

33. The method of claim 30 further comprising the step of measuring platelet aggregation based on said any further blood position change away from said respective level positions over time.

34. The method of claim 30 further comprising the step of measuring red blood cell deformability based on said any further blood position change away from said respective level positions over time.

35. A method for detecting interactions in the circulating blood of a living being caused by external factors by analyzing the viscosity of the living being's circulating blood and wherein said step of analyzing the viscosity of the living being's circulating blood comprises the steps of:

(a) providing access to the circulating blood of the living being to form an input flow of circulating blood;

(b) dividing said input flow of circulating blood into a first flow path and a second flow path into which respective portions of said input flow pass, one of said first or second flow paths including a passageway portion having some known parameters;

(c) isolating said first and second flow paths from said input flow and coupling said first and second flow paths together so that the position of the blood in each of said flow paths changes;

(d) monitoring the blood position change in said first and second flow paths over time; and (e) calculating the viscosity of the living being's circulating blood over a first shear rate range based on said blood position change and on selected known parameters of said passageway to determine a first viscosity profile.

36. The method of claim 35 further comprising the step of calculating the viscosity of the living being's circulating blood over said first shear rate and a second shear rate based on said blood position change and on said selected known parameters of said passageway to determine a second viscosity profile.

37. The method of claim 36 wherein said step of calculating the viscosity of the living being's circulating blood over said first shear rate and a second shear rate is conducted in real time.

38. The method of claim 37 further comprising the step of determining a relationship between said first viscosity profile and a horizontal line.

39. The method of claim 38 further comprising the step of determining a relationship between said first viscosity profile and said second viscosity profile.

40. The method of claim 38 wherein said step of determining a relationship between said first viscosity profile and a horizontal line comprises the steps of:
   (a) plotting the logarithm of said first viscosity profile versus the logarithm of shear rate; and
   (b) determining a first angle formed between said first viscosity profile and said horizontal line.

41. The method of claim 40 wherein step of determining a relationship between said first viscosity profile and said second viscosity profile further comprises the steps of:
   (a) plotting the logarithm of said second viscosity profile versus the logarithm of shear rate; and
   (b) determining a second angle formed between said first viscosity profile and said second viscosity profile.

42. The method of claim 37 wherein said first shear rate range is approximately $320 \, s^{-1}$ to $1 \, s^{-1}$.

43. The method of claim 37 wherein said second shear rate range is approximately $1s^{-1}$ to $0.02 \, s^{-1}$.

44. The method of claim 41 further comprising the step of determining that the living being has low hematocrit and low potential of thrombosis when said first angle is minimized and said second angle is approximately zero degrees.

45. The method of claim 41 further comprising the step of determining that the living being has high hematocrit and high potential of thrombosis when said first angle is not minimized and said second angle is greater than zero degrees.

46. The method of claim 41 further comprising the step of determining that the living being has low triglycerides and low potential of thrombosis when said first angle is minimized and said second angle is approximately zero degrees.

47. The method of claim 41 further comprising the step of determining that the living being has high triglycerides and high potential of thrombosis when said first angle is not minimized and said second angle is greater than zero degrees.

48. The method of claim 41 further comprising the step of determining that the living being has low cholesterol and low potential of thrombosis when said first angle is minimized and said second angle is approximately zero degrees.

49. The method of claim 41 further comprising the step of determining that the living being has high cholesterol and high potential of thrombosis when said first angle is not minimized and said second angle is greater than zero degrees.

50. An apparatus for detecting interactions in the circulating blood of a living being caused by external factors, said apparatus comprising:
   a lumen arranged to be coupled to the vascular system of the being;
   a pair of tubes having respective first ends and second ends, said first ends being coupled together via a capillary tube having some known parameters;
   a valve for controlling the flow of circulating blood from the being's vascular system to said pair of tubes, said valve being coupled to a second end of one of said pair of tubes and being coupled to said lumen; and
   an analyzer, coupled to said valve, for controlling said valve to permit the flow of blood into said pair of tubes whereupon the blood in each of said pair of tubes assumes a respective initial position with respect thereto, said analyzer also being arranged for operating said valve to isolate said pair of tubes from the being's vascular system so that the position of the blood in said pair of tubes changes, said analyzer also being arranged for monitoring the blood position change in said tubes and for calculating the viscosity of the living being's blood over a first shear rate range and a second shear rate range based on said blood position change and on selected known parameters of said capillary tube to determine a first viscosity profile and a second viscosity profile.

51. The apparatus of claim 50 wherein said apparatus is adapted for effecting the viscosity measurement of circulating blood of a living being in real-time.

52. The apparatus of claim 51 wherein said pair of tubes and said capillary are arranged to be pivoted around an axis as a unit.

53. The apparatus of claim 52 wherein said analyzer comprises a respective monitor for each of said pair of tubes, each of said respective monitors monitoring the blood position change in said respective tubes and each of said respective monitors being pivotal around said axis so as to remain in a fixed relationship with said pair of tubes when said pair of tubes is pivoted.

54. The apparatus of claim 53 wherein said respective monitors comprise respective light arrays and charge coupled devices (CCDs).

55. The apparatus of claim 54 wherein each of said respective light arrays comprises a plurality of light emitting diodes arranged in linear fashion to illuminate a respective tube along the length of said tube.

56. The apparatus of claim 53 wherein said pair of tubes and said capillary form a portion of a transparent cartridge that is pivotal about a horizontal axis.

57. The apparatus of claim 56 wherein said transparent cartridge and said respective monitors are mounted on a common shaft that is rotatable by a driving means.

58. The apparatus of claim 57 wherein said respective monitors comprise respective light arrays and charge coupled devices (CCDs).

59. The apparatus of claim 58 wherein each of said respective light arrays comprises a plurality of light emitting diodes arranged in linear fashion to illuminate a respective tube along the length of said tube.

60. The apparatus of claim 56 wherein said transparent cartridge is disposable.

61. The apparatus of claim 53 wherein said analyzer further comprises means for measuring platelet aggregation based on movement of said respective columns when they are pivoted.

62. The apparatus of claim 53 wherein said analyzer further comprises means for measuring red blood cell deformability based on movement of said respective columns when they are pivoted.

63. An apparatus for detecting interactions in the circulating blood of a living being caused by external factors, said apparatus comprising:
   a lumen arranged to be coupled to the vascular system of the being;
   a pair of tubes having respective first ends coupled to said lumen for receipt of circulating blood from the being, one of said pair of tubes comprising a capillary tube having some known parameters;

a valve for controlling the flow of circulating blood from the being's vascular system to said pair of tubes; and an analyzer, coupled to said valve, for controlling said valve to permit the flow of blood into said pair of tubes whereupon the blood in each of said pair of tubes assumes a respective initial position with respect thereto, said analyzer also being arranged for operating said valve to isolate said pair of tubes from the being's vascular system and for coupling said pair of tubes together so that the position of the blood in said pair of tubes changes, said analyzer also being arranged for monitoring the blood position change in said tubes and for calculating the viscosity of the living being's blood over a first shear rate range and a second shear rate range based on said blood position change and on selected known parameters of said capillary tube to determine a first viscosity profile and a second viscosity profile.

64. The apparatus of claim 63 wherein said apparatus is adapted for effecting the viscosity measurement of circulating blood of a living being in real-time.

65. The apparatus of claim 64 wherein said respective monitors comprise respective light arrays and charge coupled devices (CCDs).

66. The apparatus of claim 65 wherein each of said respective light arrays comprises a plurality of light emitting diodes arranged in linear fashion to illuminate a respective tube along the length of said tube.

67. The apparatus of claim 66 wherein said respective monitors comprise respective light arrays and charge coupled devices (CCDs).

68. The apparatus of claim 67 wherein each of said respective light arrays comprises a plurality of light emitting diodes arranged in linear fashion to illuminate a respective tube along the length of said tube.

69. A method for determining the yield stress of the circulating blood of a living being, said method comprising the steps of:

(a) providing access to the circulating blood of the living being to form an input flow of circulating blood;

(b) directing said input flow into one end of a pair of tubes coupled together via a passageway having some known parameters, said input flow passing through a first one of said pair of tubes, through said passageway and into a first portion of a second one of said pair of tubes in order to form respective columns in said first and second tubes;

(c) isolating said respective columns from said input flow so that the position of the blood in each of said columns changes;

(d) monitoring the blood position change in said respective columns of blood over time;

(e) detecting a difference between the final levels of said columns; and (f) calculating the yield stress of the blood based on said difference and on selected known parameters of said passageway.

70. The method of claim 69 wherein said step of calculating the yield stress is defined as:

$$\tau_0 = \frac{\rho g \Delta h}{\pi \phi_C L_C}$$

where $\tau_0$=yield stress
$\rho$=blood fluid density,
g=gravitational constant,
$\Delta h$=said difference between the final levels of said columns,
$\phi_c$=inside diameter of said passageway; and
$L_c$=length of said passageway.

71. An apparatus for determining the yield stress of the circulating blood of a living being, said apparatus comprising:

a lumen arranged to be coupled to the vascular system of the being;

a pair of tubes having respective first ends and second ends, said first ends being coupled together via a capillary tube having some known parameters;

a valve for controlling the flow of circulating blood from the being's vascular system to said pair of tubes, said valve being coupled to a second end of one of said pair of tubes and being coupled to said lumen; and an analyzer, coupled to said valve, for controlling said valve to permit the flow of blood into said pair of tubes whereupon the blood in each of said pair of tubes assumes a respective initial position with respect thereto, said analyzer also being arranged for operating said valve to isolate said pair of tubes from the being's vascular system so that the position of the blood in said pair of tubes changes, said analyzer also being arranged for monitoring the blood position change in said tubes over time and for detecting a difference between the final positions of the blood in said pair of tubes, said analyzer calculating the yield stress of the circulating blood based on said difference and on selected known parameters of said capillary tube.

72. The apparatus of claim 71 wherein said difference and said selected known parameters comprise the following relationship:

$$\tau_0 = \frac{\rho g \Delta h}{\pi \phi_C L_C}$$

where $\tau_0$=yield stress
$\rho$=blood fluid density
g=gravitational constant,
$\Delta h$=said difference between said final positions of the blood,
$\phi_c$=inside diameter of said capillary tube; and
$L_c$=length of said capillary tube.

73. A method for determining the yield stress of the circulating blood of a living being, said method comprising the steps of:

(a) providing access to the circulating blood of the living being to form an input flow of circulating blood;

(b) dividing said input flow of circulating blood into a first flow path and a second flow path into which respective portions of said input flow pass, one of said first or second flow paths including a passageway portion having some known parameters;

(c) isolating said first and second flow paths from said input flow and coupling said first and second flow paths together so that the position of the blood in each of said flow paths changes;

(d) monitoring the blood position change in said first and second flow paths over time;

(e) detecting a difference between the final positions of the blood in said first and second flow paths; and (f) calculating the yield stress of the blood based on said difference and on selected parameters of passageway portion.

74. The method of claim 73 wherein said step of calculating the yield stress is defined as:

$$\tau_0 = \frac{\rho g \Delta h}{\pi \phi_C L_C}$$

where $\tau_0$=yield stress $\rho$=blood fluid density g=gravitational constant, $\Delta h$=said difference between the final positions of the blood in said first and second flow paths, $\phi_c$=inside diameter of said passageway; and $L_c$=length of said passageway.

75. An apparatus for determining the yield stress of the circulating blood of a living being, said apparatus comprising:

a lumen arranged to be coupled to the vascular system of the being;

a pair of tubes having respective first ends coupled to said lumen for receipt of circulating blood from the being, one of said pair of tubes comprising a capillary tube having some known parameters;

a valve for controlling the flow of circulating blood from the being's vascular system to said pair of tubes; and an analyzer, coupled to said valve, for controlling said valve to permit the flow of blood into said pair of tubes whereupon the blood in each of said pair of tubes assumes a respective initial position with respect thereto, said analyzer also being arranged for operating said valve to isolate said pair of tubes from the being's vascular system and for coupling said pair of tubes together so that the position of the blood in said pair of tubes changes, said analyzer also being arranged for monitoring the blood position change in said tubes over time and for detecting a difference between the final positions of the blood in said pair of tubes, said analyzer calculating the yield stress of the circulating blood based on said difference and on selected known parameters of said capillary tube.

76. The apparatus of claim 75 wherein said difference and said selected known parameters comprise the following relationship:

$$\tau_0 = \frac{\rho g \Delta h}{\pi \phi_C L_C}$$

where $\tau_0$=yield stress $\rho$=blood fluid density g=gravitational constant, $\Delta h$=said difference between the final positions of the blood in said pair of tubes, $\phi_c$=inside diameter of said capillary tubes; and $L_c$=length of said capillary tube.

77. A method for determining the effects of drugs, introduced into a living being, that are designed to treat a condition of the living being, said method comprising the step of analyzing the viscosity of the living being's circulating blood and wherein said step of analyzing the viscosity of the living being's circulating blood comprises:

(a) determining the viscosity of the living being's circulating blood over a first shear rate range to determine a first viscosity profile; and (b) determining the viscosity of the living being's blood over the first shear rate range and a second shear rate range to determine a second viscosity profile.

78. The method of claim 77 wherein said steps (a) and (b) are conducted in real time.

79. The method of claim 78 further comprising the step of determining a relationship between said first viscosity profile and a horizontal line.

80. The method of claim 79 further comprising the step of determining a relationship between said first viscosity profile and said second viscosity profile.

81. The method of claim 79 wherein said step of determining a relationship between said first viscosity profile and a horizontal line comprises the steps of:

(a) plotting the logarithm of said first viscosity profile versus the logarithm of shear rate; and (b) determining a first angle formed between said first viscosity profile and said horizontal line.

82. The method of claim 81 wherein step of determining a relationship between said first viscosity profile and said second viscosity profile further comprises the steps of:

(a) plotting the logarithm of said second viscosity profile versus the logarithm of shear rate; and (b) determining a second angle formed between said first viscosity profile and said second viscosity profile.

83. The method of claim 78 wherein said first shear rate range is approximately 320 $s^{-1}$ to 1 $s^{-1}$.

84. The method of claim 78 wherein said second shear rate range is approximately 1$s^{-1}$ to 0.02 $s^{-1}$.

\* \* \* \* \*